United States Patent

Laird et al.

Patent Number: 5,833,634
Date of Patent: Nov. 10, 1998

[54] TISSUE EXAMINATION

[75] Inventors: John D. Laird, Boxford; David E. Coats, Newton; Michael J. Iorio, Framington; Jonathan D. Schiff, Andover; Carl J. Wisnosky, Spencer; Steven B. Woolfson, Brookline, all of Mass.

[73] Assignee: UroMed Corporation, Needham, Mass.

[21] Appl. No.: 556,161

[22] Filed: Nov. 9, 1995

[51] Int. Cl.⁶ .................................................. A61B 5/103
[52] U.S. Cl. ............................................................ 600/587
[58] Field of Search .................................. 128/774, 782, 128/744, 630

[56] References Cited

U.S. PATENT DOCUMENTS

| | | | |
|---|---|---|---|
| Re. 30,446 | 12/1980 | Meyers et al. | 128/736 |
| Re. 32,000 | 10/1985 | Sagi | 128/736 |
| 3,154,789 | 11/1964 | Lewis, Jr. | 2/104 |
| 3,308,476 | 3/1967 | Kleesattel . | |
| 3,323,352 | 6/1967 | Branson . | |
| 3,744,490 | 7/1973 | Fernandez | 128/2.05 |
| 3,847,139 | 11/1974 | Flam | 128/2 H |
| 3,854,471 | 12/1974 | Wild | 128/2 V |
| 3,880,145 | 4/1975 | Blick | 128/2.05 |
| 3,970,862 | 7/1976 | Edelman et al. | 307/88 ET |
| 3,972,227 | 8/1976 | Tomilov | 73/67.7 |

(List continued on next page.)

FOREIGN PATENT DOCUMENTS

PCT/US96/
17173  10/1996  European Pat. Off. .
2 086 575 A  5/1982  United Kingdom .

OTHER PUBLICATIONS

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast–Transfer Efficiency in Elastography: an Analytic Study", 1996, Ultrasound in Med. & Biol., vol. 22, No. 4, pp.463–470.

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp.111–117.

G.I. Pressman et al., "A Transducer for the Continuous External Measurement of Arterial Blood Pressure", 1960s, IEEE Transactions on Bio–Medical Electronics.

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel J. Med. Sci., pp. 859–864, Israel.

R.G. Stevens et al., "The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

*Primary Examiner*—Max Hindenburg
*Assistant Examiner*—Pamela L. Wingood
*Attorney, Agent, or Firm*—Fish & Richardson P.C.

[57] ABSTRACT

Tissue is examined with a device that includes one or more transducer elements, each of which generates a signal in response to force imposed on the transducer element in accordance with varying properties of an underlying tissue structure as the transducer element is pressed against and moved over the tissue. The tissue examination device further includes circuitry for detecting a variation in the signals as an indication of a composition of the underlying tissue structure.

104 Claims, 15 Drawing Sheets

U.S. PATENT DOCUMENTS

| | | | |
|---|---|---|---|
| 3,996,922 | 12/1976 | Basham | 128/2 R |
| 4,001,951 | 1/1977 | Fasse | 35/17 |
| 4,023,562 | 5/1977 | Hynecek et al. | 128/2.05 E |
| 4,025,165 | 5/1977 | Sollish et al. | 350/161 S |
| 4,132,224 | 1/1979 | Randolph | 128/2 S |
| 4,134,218 | 1/1979 | Adams et al. | 35/17 |
| 4,135,497 | 1/1979 | Meyers et al. | 128/2 H |
| 4,144,877 | 3/1979 | Frei et al. | 128/2 S |
| 4,159,640 | 7/1979 | Leveque et al. | 73/81 |
| 4,190,058 | 2/1980 | Sagi | 128/736 |
| 4,212,306 | 7/1980 | Mahmud | 128/665 |
| 4,219,708 | 8/1980 | Rubey | 200/61.47 |
| 4,250,894 | 2/1981 | Frei et al. | 128/774 |
| 4,286,602 | 9/1981 | Guy | 128/665 |
| 4,291,708 | 9/1981 | Frei et al. | 128/734 |
| 4,458,694 | 7/1984 | Sollish et al. | 128/734 |
| 4,503,865 | 3/1985 | Shishido | 128/774 |
| 4,524,778 | 6/1985 | Brown, Jr. et al. | 128/736 |
| 4,555,953 | 12/1985 | Dario et al. | 73/862.04 |
| 4,570,638 | 2/1986 | Stoddart et al. | 128/665 |
| 4,600,011 | 7/1986 | Watmough | 128/664 |
| 4,641,659 | 2/1987 | Sepponen | 128/653 |
| 4,641,661 | 2/1987 | Kalarickal | 128/744 |
| 4,651,749 | 3/1987 | Sagi | 128/736 |
| 4,657,021 | 4/1987 | Perry et al. | 128/630 |
| 4,729,378 | 3/1988 | Trittenbass | 128/645 |
| 4,737,109 | 4/1988 | Abramson | 434/267 |
| 4,768,516 | 9/1988 | Stoddart et al. | 128/665 |
| 4,774,961 | 10/1988 | Carr | 128/736 |
| 4,793,354 | 12/1988 | Wright et al. | 128/630 |
| 4,807,637 | 2/1989 | Bjorkhom | 128/664 |
| 4,810,875 | 3/1989 | Wyatt | 250/227 |
| 4,817,623 | 4/1989 | Stoddart et al. | 128/665 |
| 4,873,982 | 10/1989 | Morrison | 128/630 |
| 5,010,772 | 4/1991 | Bourland et al. | 73/862.04 |
| 5,012,817 | 5/1991 | Zeilinski et al. | 128/744 |
| 5,079,698 | 1/1992 | Grenier et al. | 364/413.13 |
| 5,099,848 | 3/1992 | Parker et al. | 128/661.07 |
| 5,140,989 | 8/1992 | Lewis et al. | 128/665 |
| 5,143,079 | 9/1992 | Frei et al. | 128/734 |
| 5,212,637 | 5/1993 | Saxena | 364/413.26 |
| 5,221,269 | 6/1993 | Miller et al. | 604/281 |
| 5,265,612 | 11/1993 | Sarvazyan et al. | 128/660.01 |
| 5,301,681 | 4/1994 | DeBan et al. | 128/736 |
| 5,301,682 | 4/1994 | Debbas | 128/737 |
| 5,373,612 | 12/1994 | Wild | 128/660.9 |
| 5,524,636 | 6/1996 | Sarvazyan et al. | |
| 5,678,565 | 10/1997 | Sarvazyan | |

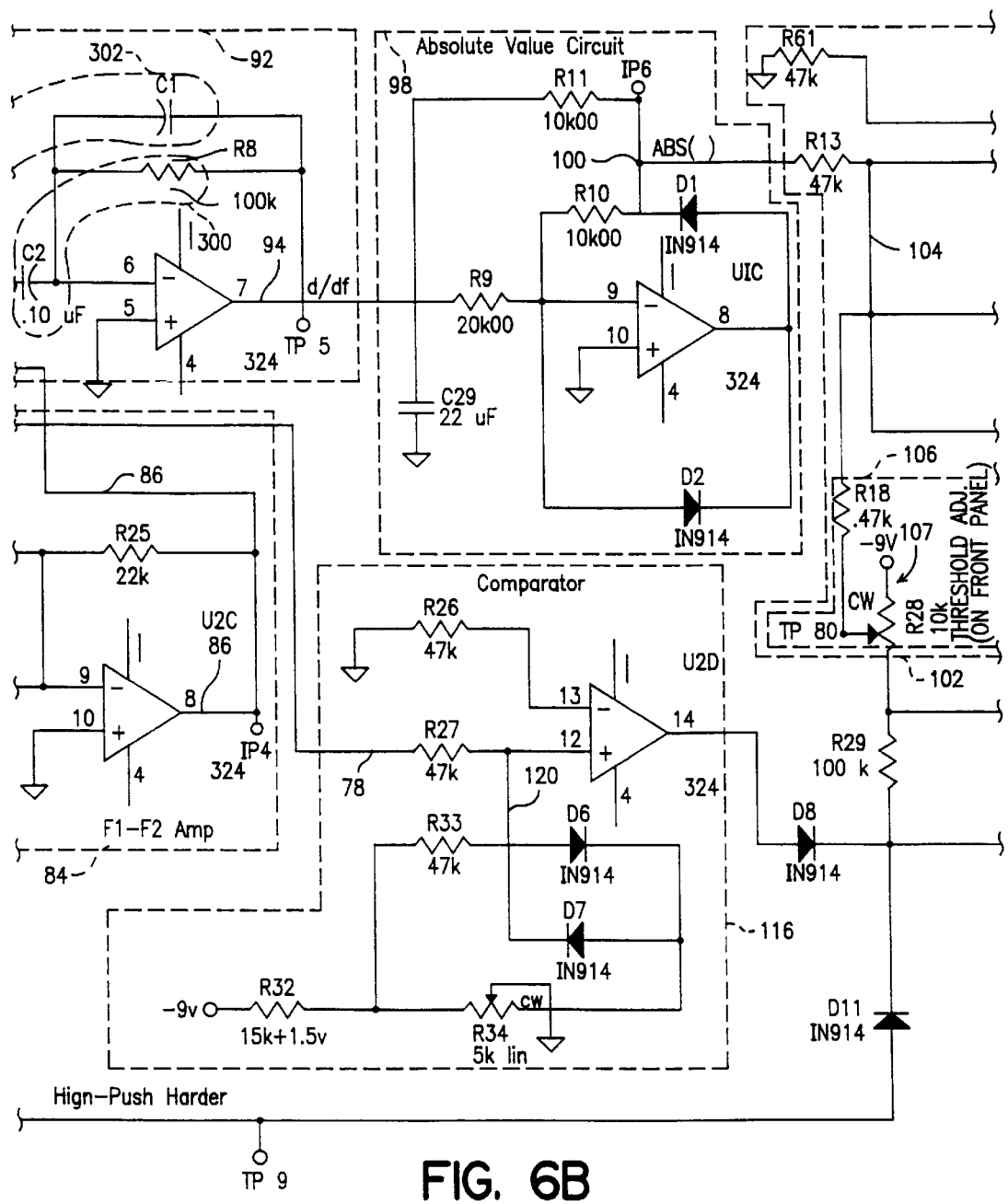

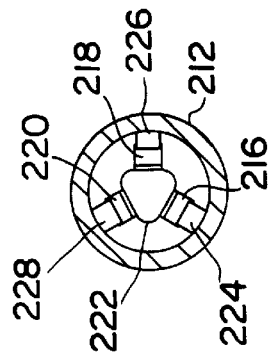
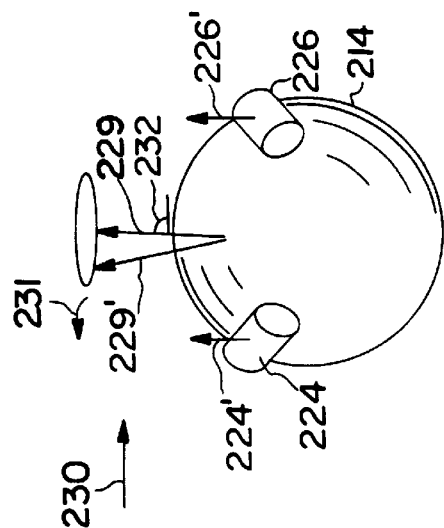
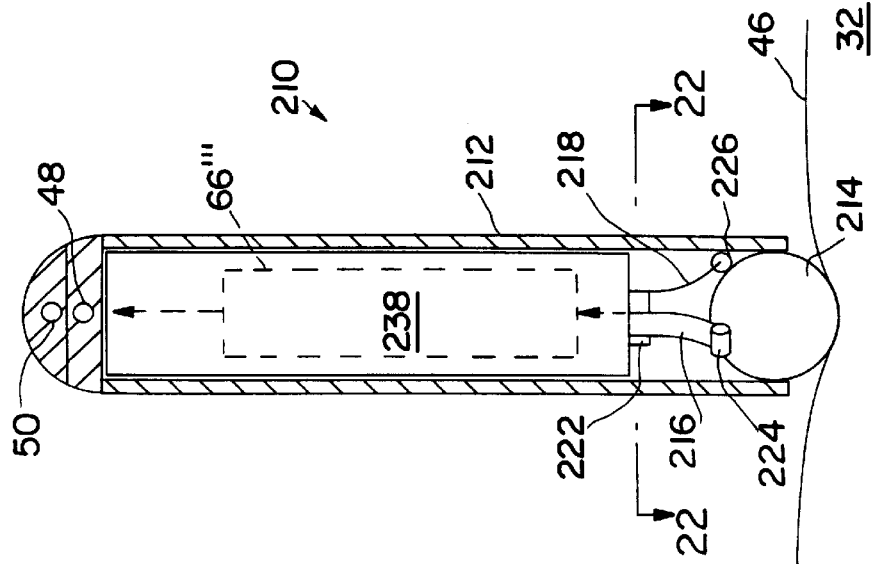
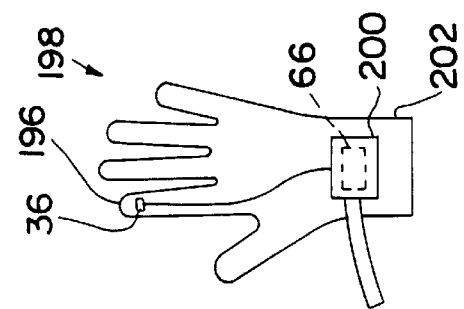

TISSUE EXAMINATION

BACKGROUND

This invention relates to tissue examination.

In order to detect localized areas of stiffer tissue (e.g., lumps) within soft tissue (e.g., breast tissue), a detection device (e.g., human fingers) is typically coupled with the lump through the skin and tissue surrounding the lump. At low stress levels, soft tissue is very elastic and absorbs the strains of slight deformations in the tissue. However, as the stress level increases, soft tissue increases in stiffness providing improved coupling between the surface of the tissue and any lump within the tissue.

For example, to provide this increased stress level, breast self-examinations are performed manually by firmly pressing on the breast with three fingers while moving the fingers in a circular palpating motion. Typically, women using manual breast self-examinations are not able to detect lumps of less than 1 cm in diameter. Breast self-examinations are inherently subjective with efficacy varying with the skill and training of the examiner.

Referring to FIG. 1, one known device 10 for enabling a more objective detection of localized areas of stiffer tissue (e.g., lumps) in soft tissue 12 presses at least one pair of transducer elements 14, 16 against the soft tissue. Each transducer element generates an electrical signal that is proportional to the force imposed on the transducer element. When the transducer pair is positioned across the boundary 18 of a lump 20 within the soft tissue, transducer element 16, lying over the lump, generates an electrical signal indicating the detection of a larger force than transducer element 14, lying over soft tissue alone. Device 10 calculates the difference between the two electrical signals to determine the presence of lump 20. Generally, the user does not know whether the tissue being examined has any lumps. The user positions and repositions device 10 in an effort to place the transducer elements 14, 16 directly across a boundary of a lump.

SUMMARY

One general aspect of this invention features examining tissue with a device that includes a transducer element for generating a signal in response to force imposed on the transducer element in accordance with the varying properties of an underlying tissue structure as the transducer element is pressed against and moved over the tissue, and circuitry for detecting a variation in the signal as an indication of a composition of the underlying tissue structure.

Implementations may include one or more of the following features.

A processor determines whether the transducer element has been moved over a localized area of stiffer tissue (such as a lump) within the underlying tissue structure (e.g., breast tissue). This is done by comparing the detected variation in the signal to a threshold—which may be constant, variable, or a selected signal pattern. When the detected variation exceeds the threshold, the user is notified that a localized area of stiffer tissue has been detected. For example, a light emitting diode is illuminated and/or a sound generator is actuated.

A pressure sensing circuit detects whether the force imposed on the transducer element exceeds a minimum and/or maximum threshold (either or both of which may be variable). The user is notified (such as with a light or sound alarm) when the force imposed on the transducer element is below the minimum threshold and/or above the maximum threshold.

The variation in the detected signal may be the rate of change of the signal generated by the transducer element. The transducer element is, for example, a carbon microphone. The detecting circuitry and the processor may include analog circuitry, a microprocessor, or both.

In one embodiment, a single transducer element is used. In this case, the rate of change of the transducer-generated signal is determined by a dual differentiator circuit, which takes a second derivative of the transducer-generated signal. An integrator may be provided for integrating the second derivative obtained by the dual differentiator circuit, or not.

In another general aspect of the invention, the tissue examination device includes multiple transducer elements, and variations in the signals generated by the multiple transducer elements are detected as an indication of a composition of the underlying tissue structure.

Implementations may include one or more of the following features.

The difference between the signals generated by the transducer elements is determined (e.g., one signal is subtracted from the other), and the variation in the difference is detected as the indication of the underlying tissue structure composition. The detected variation is compared to a constant or variable threshold. Alternatively, the variation may be compared with a predetermined pattern to determine whether at least one transducer element has been moved over the localized area of stiffer tissue within the underlying tissue structure. The detected variation can also be compared to predetermined patterns to determine the type of localized area of stiffer tissue over which the device has been moved.

The rate of change of the difference between the transducer-generated signals is determined by a differentiator, which takes a derivative of the difference between the signals generated by the transducer elements to detect the rate of change of the difference between the signals generated by the transducer elements. The detecting circuitry may also include an integrator for integrating the derivative.

The tissue examination device can be housed in any way suitable for moving the transducer elements over the tissue. For example, the tissue examination device may be disposed in a hand-held housing or on a glove, adhesive strip, etc. to allow the user to move the transducer elements manually over the tissue. The device may include a roller ball assembly for facilitating movement. Alternatively, the tissue examination device may include a mechanism, attached to the transducer elements, for automatically moving the transducer elements over the tissue.

The transducer elements may be configured as multiple pairs of transducer elements and/or multiple arrangements of two pairs of transducer elements in orthogonal configurations. In this case, the difference between the signals generated by each pair of transducer elements is determined, and the variations in these differences are detected to provide an indication of the composition of the underlying tissue structure. A velocity measuring device may also be included for measuring the velocity with which the transducer elements are moved over the tissue. In this case, the variations in the differences between the signals of each pair of transducer elements are coordinated with signals produced by the velocity measuring device to provide spacial information regarding the location of the localized area of stiffer tissue within the underlying tissue structure, which is displayed to the user on a display device.

In another general aspect, the invention features a roller ball assembly including a roller ball and multiple transducer elements, in contact with the roller ball, for generating signals in response to forces imposed on the transducer elements as the roller ball is pressed against and moved over the tissue. The assembly further includes circuitry for determining a resulting force vector and force vector angle from the signals generated by the transducer elements as an indication of a composition of the underlying tissue structure.

Implementations include one or more of the following features.

The assembly includes circuitry for detecting a variation in the force vector angle as an indication of a composition of the underlying tissue structure. The transducer elements are strain instrumented springs.

Advantages of the invention include one or more of the following. Generally, the amount of tissue to be examined is much larger than the size of any possible localized areas of stiffer tissue in the tissue. Moving one or more transducer elements over the tissue to be examined increases the likelihood that a boundary of a localized area of stiffer tissue in the underlying tissue will be crossed and the localized area of stiffer tissue will be detected. Moving one or more transducer elements also allows more tissue area to be covered in a smaller amount of time.

The difference in the force imposed on a transducer element as it crosses the boundary of a localized area of stiffer tissue is typically small and may be difficult to detect. A variation, for instance, the rate of change, in the force imposed on one transducer element or in the difference in force imposed on multiple transducer elements, however, may be large as one or more transducer elements pass over the boundary of a localized area of stiffer tissue within the underlying tissue. Thus, detecting a variation in the signal generated by one or more transducer elements enhances the detection of localized areas of stiffer tissue. Furthermore, detecting a predetermined pattern in a variation of the signal generated by one transducer element or in a variation of the difference between signals generated by multiple transducer elements may be used to determine the type of localized area of stiffer tissue that has been detected.

Taking the difference between signals generated by closely spaced transducer elements removes the effects of the absolute force applied by the user to the tissue examination device because the absolute force will be imposed substantially equally on both transducer elements.

The user is also not required to interpret complex data to detect possible localized areas of stiffer tissue. Instead, the user is notified of possible localized areas of stiffer tissue through the flash of a light, a tone, or vibration. Using multiple transducer assemblies increases the required signal processing circuitry but may decrease the amount of time required to thoroughly examine a region of soft tissue, e.g., a breast. Additionally, through the use of a microprocessor, a digital signal processor, or a similar device, the data from an array of transducer assemblies may be acquired and coordinated with respect to the locations of the transducer assemblies to map the location and configuration of any detected localized area of stiffer tissue or boundary of a localized area of stiffer tissue. The use of an array of transducer elements also permits more sophisticated detection methods, as well as, strategies for reducing the incidence of false positive and false negative indications.

The tissue examination device is particularly useful in examining tissue using a palpating motion. For instance, to find localized areas of stiffer tissue (e.g., lumps) during breast self-examinations, one or more transducer elements may be moved in a palpating motion similar to that used during normal breast palpation. Additionally, the transducer elements enhance the effectiveness of self-examinations by detecting localized areas of stiffer tissue that are smaller than those typically detectable by normal breast palpation (e.g., 1 cm).

Other advantages and features will become apparent from the following description and from the claims.

DESCRIPTION

FIGS. 6A–6C are schematic diagrams of the block diagram of FIG. 5.

FIG. 6 shows the interrelationship between FIGS. 6A–6C.

FIG. 20 is a plan view of a tissue examination device mounted to a glove.

FIGS. 21 and 22 are cross-sectional side and top views, respectively, of a roller ball tissue examination device.

FIG. 23 is a perspective view of a roller ball and two rollers.

Figure 2:
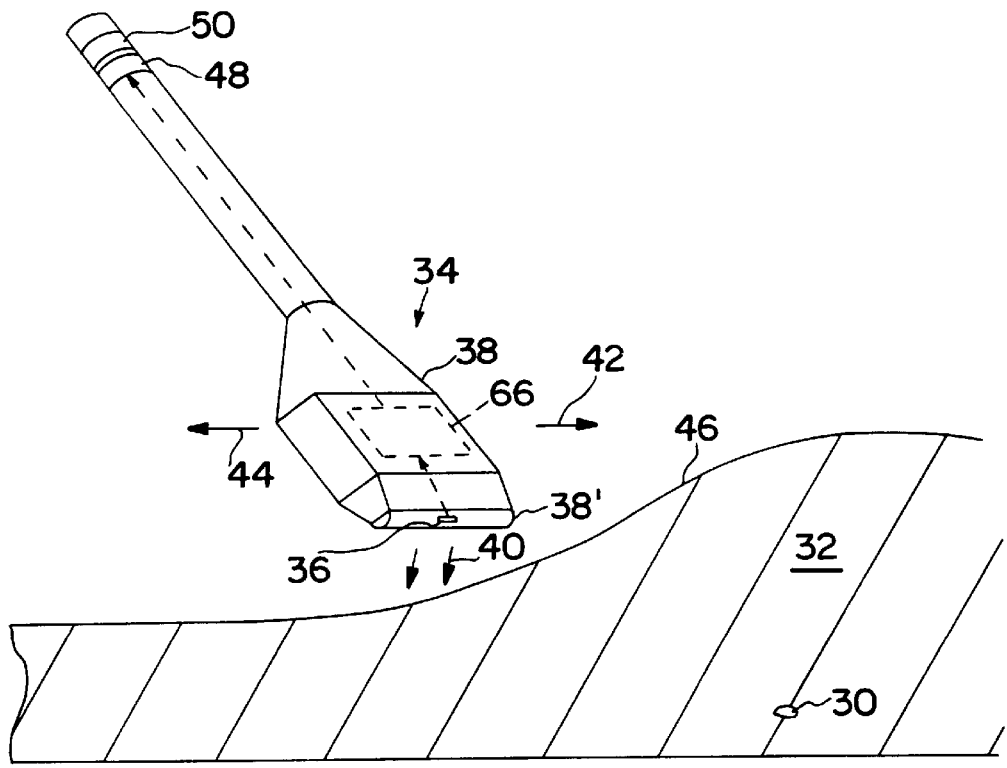
FIGS. 2 and 3 are perspective views showing the use of a tissue examination device.
Figure 3:
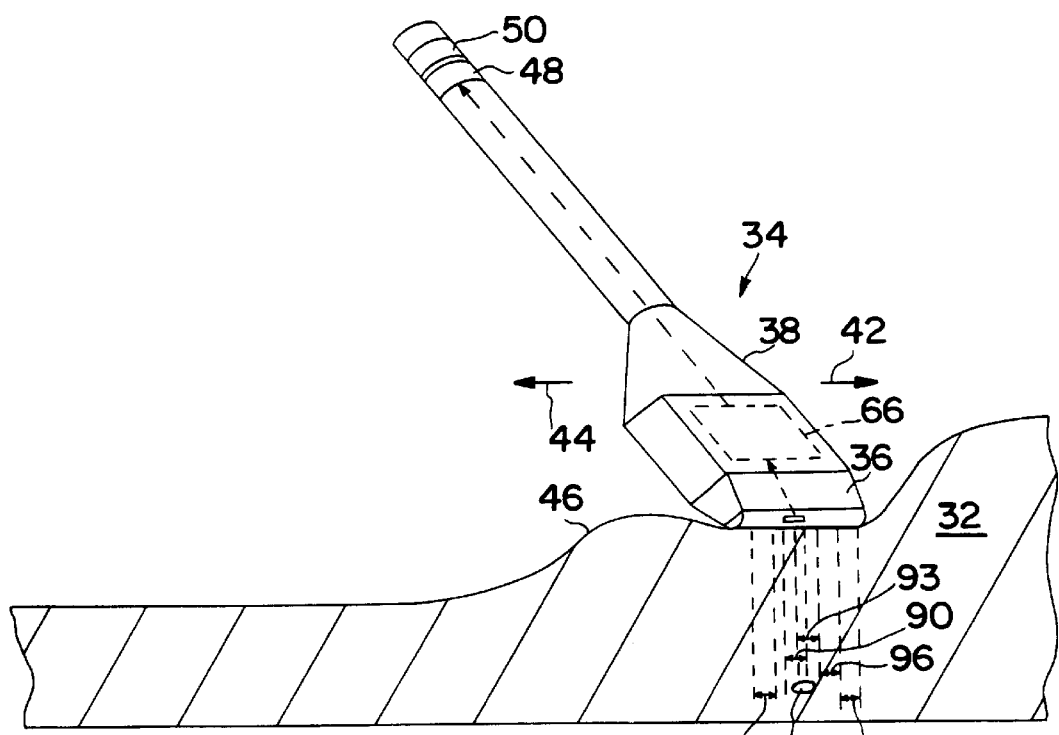

Referring to FIGS. 2 and 3, to detect localized areas of stiffer tissue, e.g., lump 30, in soft tissue 32, e.g., breast tissue, tissue examination device 34 includes a transducer assembly 36 mounted on one end of a housing 38 and a signal processor 66 (shown in FIGS. 5,6 and 6a–6c, discussed below) for detecting lump 30 based on electrical signals produced by transducer assembly 36 as it is pressed against (arrows 40) and moved along (arrows 42 and 44) a surface 46 of the tissue. Tissue examination device 34 also includes a pair of light emitting diodes (LEDs) 48, 50 at the opposite end of housing 38 and controlled by signal processor 66 for providing the user with feedback during the examination.

The operation of tissue examination device 34 is described in detail below, but briefly, if signal processor 66 detects a localized area of stiffer tissue, such as lump 30, it illuminates LED 50 (and optionally emits a sound) to notify the user that a lump may be present. The user may perform a manual examination of the tissue with his/her fingers before (or simultaneously with) the transducer examination. The user may then re-perform a manual examination of the tissue with his/her fingers as a double check and/or see a doctor for further examination. If the user is not pressing device 34 against the tissue with sufficient pressure to efficiently couple transducer assembly 34 to lump 30 or other possible localized areas of stiffer tissue within tissue 32, signal processor 66 illuminates LED 48 (and optionally emits a sound) as a notification to the user that additional pressure is required.

Figure 1:
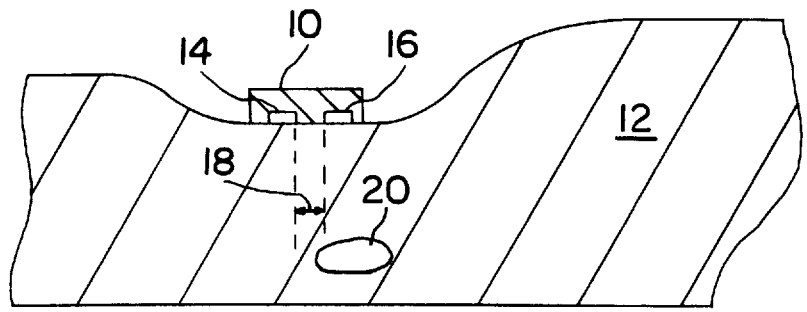
FIG. 1 is a cross-sectional side view of a pair of transducer elements.
Figure 4:
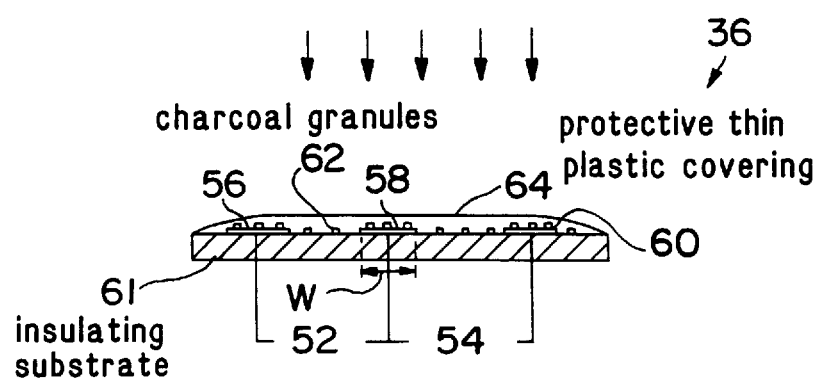
FIG. 4 is a cross-sectional side view of a transducer assembly of the tissue examination device of FIGS. 2 and 3.

Referring also to FIG. 4, transducer assembly 36 includes two transducer elements 52, 54. Transducer elements 52, 54 are in effect carbon microphones. Each transducer element includes two electrode strips: element 52 includes electrode strips 56 and 58; and element 54 includes electrode strips 58 and 60. Electrode strips 56, 58, and 60 are mounted on an insulating substrate 61, covered with a thin layer, e.g., 0.010", of activated charcoal granules 62, and then sealed with a thin, e.g., 0.005", plastic cover 64.

The resistance between each pair of electrodes 56 and 58, and 58 and 60 decreases as the force imposed on each transducer element 52, 54 increases. Force over the finite area of the transducer elements is equivalent to the pressure/stress imposed on the transducer elements. Therefore, the term "force," as used herein, includes both force and pressure. Generally, the force imposed on transducer elements 52, 54 increases when the element passes over localized areas of stiffer tissue (e.g., lump 30, milk ducts, scar tissue, ribs, etc.) within or below tissue 32. Consequently, as device 34 is pressed against and moved along tissue 32, the force imposed on transducer elements 52, 54 and, thus, the resistance of the transducer elements, varies in accordance with the underlying tissue structure.

Figure 5:
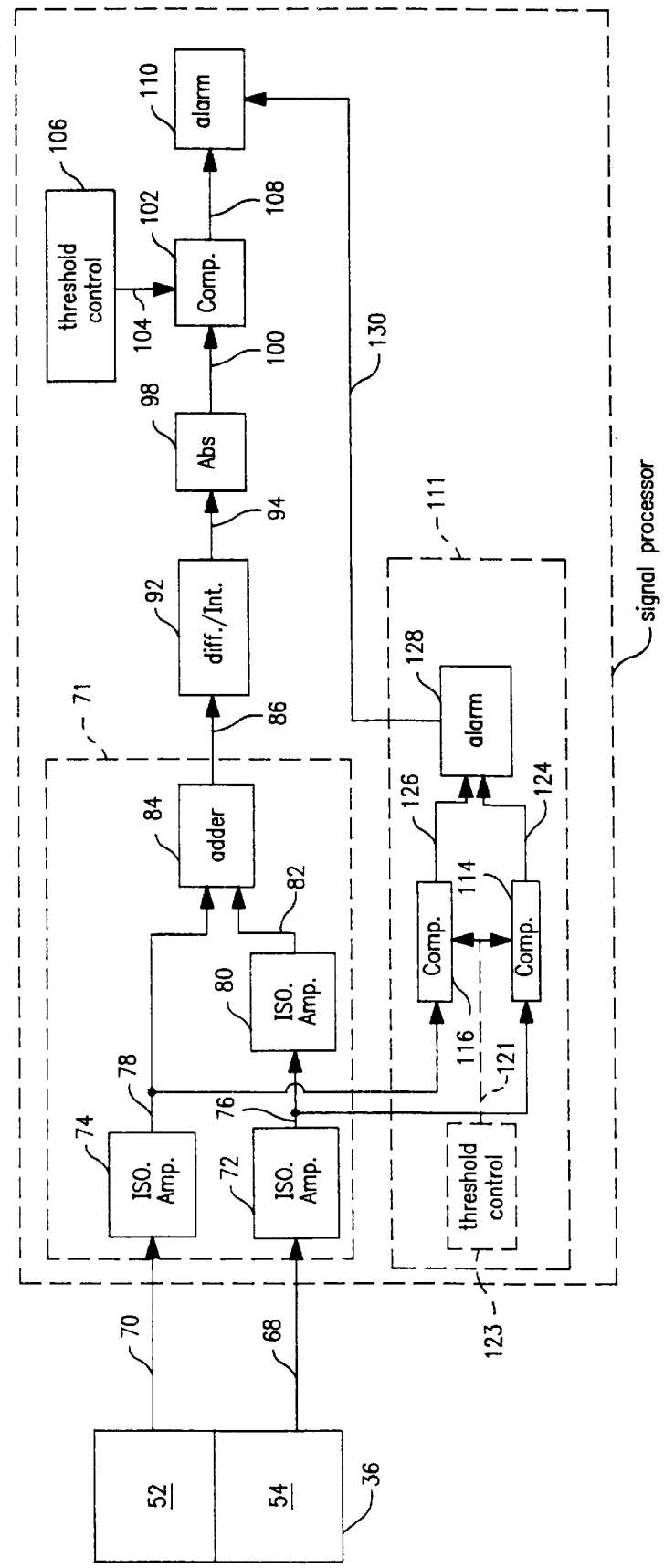
FIG. 5 is a block diagram of a signal processor of the tissue examination device of FIGS. 2 and 3 and the transducer assembly of FIG. 4.

Referring to FIG. 5, signal processor 66 receives the electrical signals indicative of force from transducer assembly 36 and determines whether a possible localized area of stiffer tissue is within tissue 32 and whether sufficient pressure is being applied between transducer assembly 36 and tissue 32. More specifically, each transducer element 54, 52 sends an electrical signal 68, 70, respectively, that is related to the force imposed on each transducer element, to subtractor 71 which determines the difference in the force imposed on each transducer element 52, 54 and generates difference signal 86. Because the two transducer elements are closely spaced (e.g., 0.020", i.e., width W, FIG. 4, of electrode strip 58), determining the difference in force imposed on each transducer element 52, 54 removes the contributions of absolute force level (i.e., the pressure applied by the user to tissue examination device 34) from difference signal 86.

Differentiator/integrator 92 (diff./int.) operates on difference signal 86 to provide an enhanced signal 94 representing the rate of change of the difference in force imposed on the transducer elements. As transducer elements 52, 54 cross over a boundary of a localized area of stiffer tissue, the difference in force imposed on transducer elements 52, 54 may be small. However, the rate of change of the difference in force imposed on transducer elements 52, 54 is generally large as the transducer elements cross over a boundary of a localized area of stiffer tissue.

Differentiator 300 (R8/C2/U1B, FIG. 6B) within differentiator/integrator 92 detects the large rate of change in difference signal 86 but is, in effect, a noise enhancing unit. Thus, enhanced signal 94 is also integrated by integrator 302 (R7/C1/U1B, FIG. 6B) within differentiator/integrator 92 to reduce the noise enhancing effect of differentiator 300. Differentiator/integrator 92 performs as a combination of a low-pass filter with a cut-off frequency determined by the R-C combination of R8/C1/U1B in FIG. 6B, together with a high-pass filter with a cut-off frequency determined by the R-C combination of R7/C2/U1B in FIG. 6B. The net result of the superposition is a frequency response curve of the type shown in FIG. 11.

Enhanced signal 94 produced by differentiator/integrator 92 is operated on by absolute value circuit 98, and output signal 100 of absolute value circuit 98 is operated on by comparator 102. Comparator 102 compares output signal 100 to threshold signal 104. If output signal 100 exceeds threshold signal 104, then tissue examination device 34 has detected a possible localized area of stiffer tissue (e.g., lump 30, FIG. 3) and alarm 110 notifies the user.

The threshold is used to avoid false positive alarms. Soft tissue, for example, breast tissue, normally varies in composition, having varying properties, e.g., elastic properties. Some areas of gradually varying properties, that is, areas without sharp boundaries, are expected. These areas cause only a small rate of change in the force difference between transducer elements 52, 54, and, as a result, output signal 100 remains low.

Conversely, more sharply bounded areas (i.e., lumps) cause large rates of change in the force difference between transducer elements 52, 54 and output signal 100 increases in value. To avoid notifying the user that tissue with gradually varying properties has been detected, the threshold signal is set at a value which is larger than the value expected for output signal 100 when transducer assembly 36 passes over gradually varying areas. Care must be taken that the threshold signal is not set so high as to mask (i.e., prevent detection of) localized areas of stiffer tissue of concern.

Signal processor 66 also includes pressure detector 111 for determining whether sufficient pressure is being applied by the user to tissue examination device 34 (FIG. 3). Electrical signals 76, 78 are inversely related (described below) to the force imposed on transducer elements 54, 52, respectively. Hence, as the forces imposed on transducer elements 54, 52 decrease, the values of electrical signals 76, 78 increase. Comparators 114, 116 compare electrical signals 76, 78, respectively, to a threshold signal (e.g., 121). If either electrical signal 76 or 78 exceeds threshold signal 121, then insufficient pressure is being applied between transducer assembly 36 and tissue 32 and alarm 128 notifies the user.

FIGS. 6 and 6A–6C illustrates signal processor 66 in greater detail. Signals 68, 70, from transducer elements 54, 52, respectively, are negative voltage signals and are operated on by isolation amplifiers 72, 74, respectively. Isolation amplifiers 72, 74 electrically isolate signals 68, 70 from each other and invert signals 68, 70 such that resulting output signals 76, 78, are positive voltage signals which are inversely related to the force imposed on transducer elements 54, 52, respectively. Signal 76 is operated on by a second isolation amplifier 80 which re-inverts signal 76 such that resulting output signal 82 is again a negative voltage signal and related (i.e., approaching zero as force increases) to the force imposed on transducer element 54.

Signals 78 and 80 are summed by adder 84, thereby deriving difference signal 86. Because signal 78 is inversely related to the force imposed on transducer element 52 while signal 80 is related to the force imposed on transducer element 54, adder 84, in effect, takes the difference between signals 78 and 80. Hence, difference signal 86 represents the difference in force imposed on transducer elements 52, 54.

When transducer assembly 36 is stationary, difference signal 86 represents the difference in force ($\Delta f$) imposed on transducer elements 52, 54 over the difference in distance ($\Delta x$) between transducer elements 52, 54. The difference in distance ($\Delta x$) is equal to the width W, FIG. 4, of electrode strip 58. When transducer assembly 36 is moved over tissue 32 (FIG. 3), difference signal 86 represents the time course of difference in force imposed on transducer elements 52, 54. For localized areas of stiffer tissue (such as lump 30) which are larger in diameter than width W of electrode strip 58, difference signal 86 approximates the first spatial derivative of force (df/dx) imposed on transducer elements 52, 54 modified by a simple Galilean transformation with velocity (dx/dt), approximately:

$$(\Delta f/\Delta x)(dx/dt) \approx (df/dx)(dx/dt) = df/dt.$$

Consequently, when transducer assembly 36 is stationary, difference signal 86 remains constant because transducer elements 52, 54 remain over the same tissue structure, resulting in no change in the difference in force imposed on transducer elements 52, 54 over time. However, as transducer assembly 36 is moved (arrows 42, 44, FIG. 3), difference signal 86 varies as transducer elements 52, 54 pass over underlying tissue structure having different compositions and properties.

Figure 7:
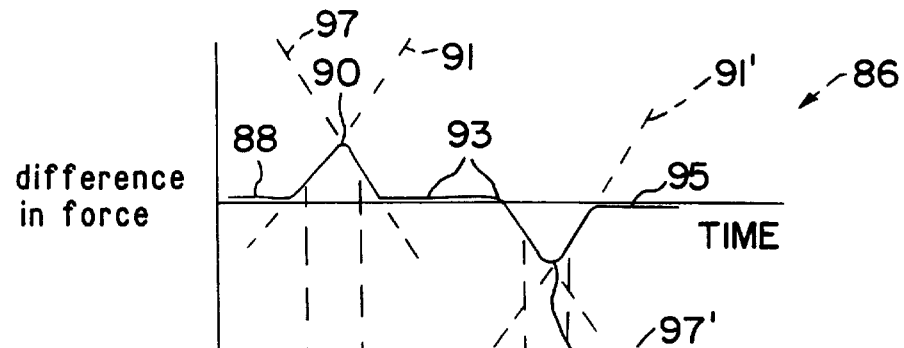
FIGS. 7–12 are graphs useful in understanding the operation of the tissue examination device of FIGS. 2 and 3.

FIG. 7 is a graph of difference signal 86 with respect to time. Referring also to FIG. 3, the difference in force imposed on transducer elements 52, 54 when transducer elements 52, 54 are both over soft tissue (positions 88 and 95) or both over lump 30 (position 93) is very small. Conversely, the difference in force imposed on transducer elements 52, 54 is larger when transducer element 52 is over lump 30 while transducer element 54 is over soft tissue (position 90) or, oppositely, transducer element 54 is over lump 30 while transducer element 52 is over soft tissue (position 96).

As transducer elements 52, 54 move from position 88 to position 90 (or from position 96 to position 95), the rate of change (slopes 91 and 91') of difference signal 86 increases rapidly. Similarly, as transducer elements 52, 54 from position 90 to position 93 (or from position 93 to position 96), the rate of change (slopes 97 and 97') of difference signal 86 decreases rapidly.

Referring back to FIGS. 6, 6A and 6B difference signal 86 is operated on by differentiator/integrator 92 which generates enhanced signal 94, approximately:

$$d/dt(df/dt) = d^2f/dt^2.$$

Figure 8:
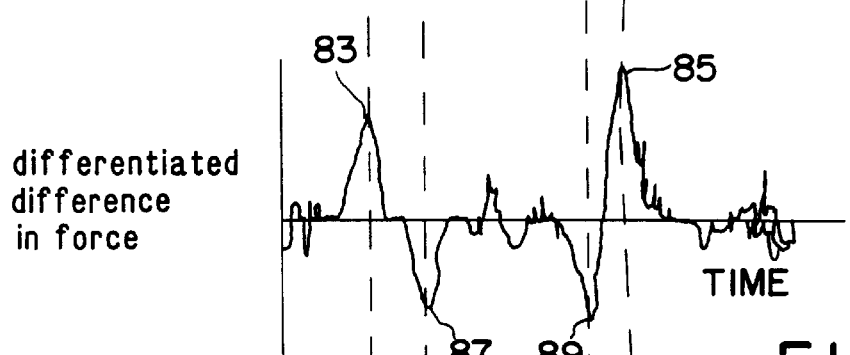

FIG. 8 is a graph of differentiated difference signal 86 with respect to time. Differentiator 300 (FIG. 6B) generates peaks 83 and 85 in response to large increases (slopes 91 and 91', FIG. 7) in the rate of change of difference signal 86 and peaks 87 and 89 in response to large decreases (slopes 97 and 97') in the rate of change of difference signal 86.

Figure 9:
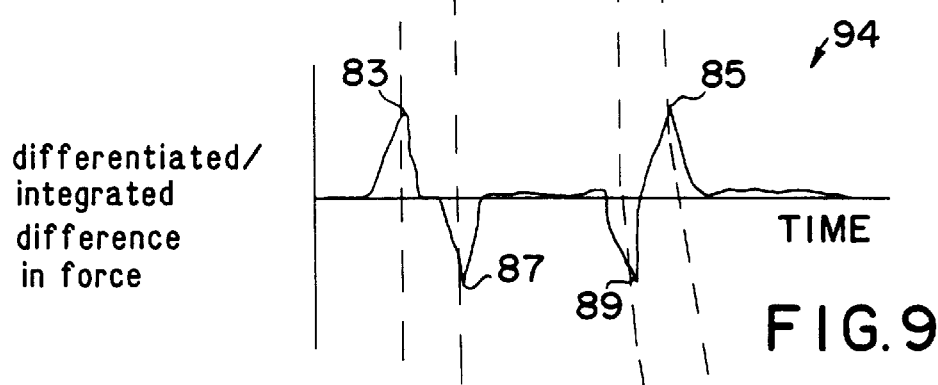

FIG. 9 is a graph of enhanced signal 94 driven by differentiator/integrator 92 (FIG. 6B). As shown, integrator 302 reduces the noise enhancing effect of differentiator 300.

Figure 11:
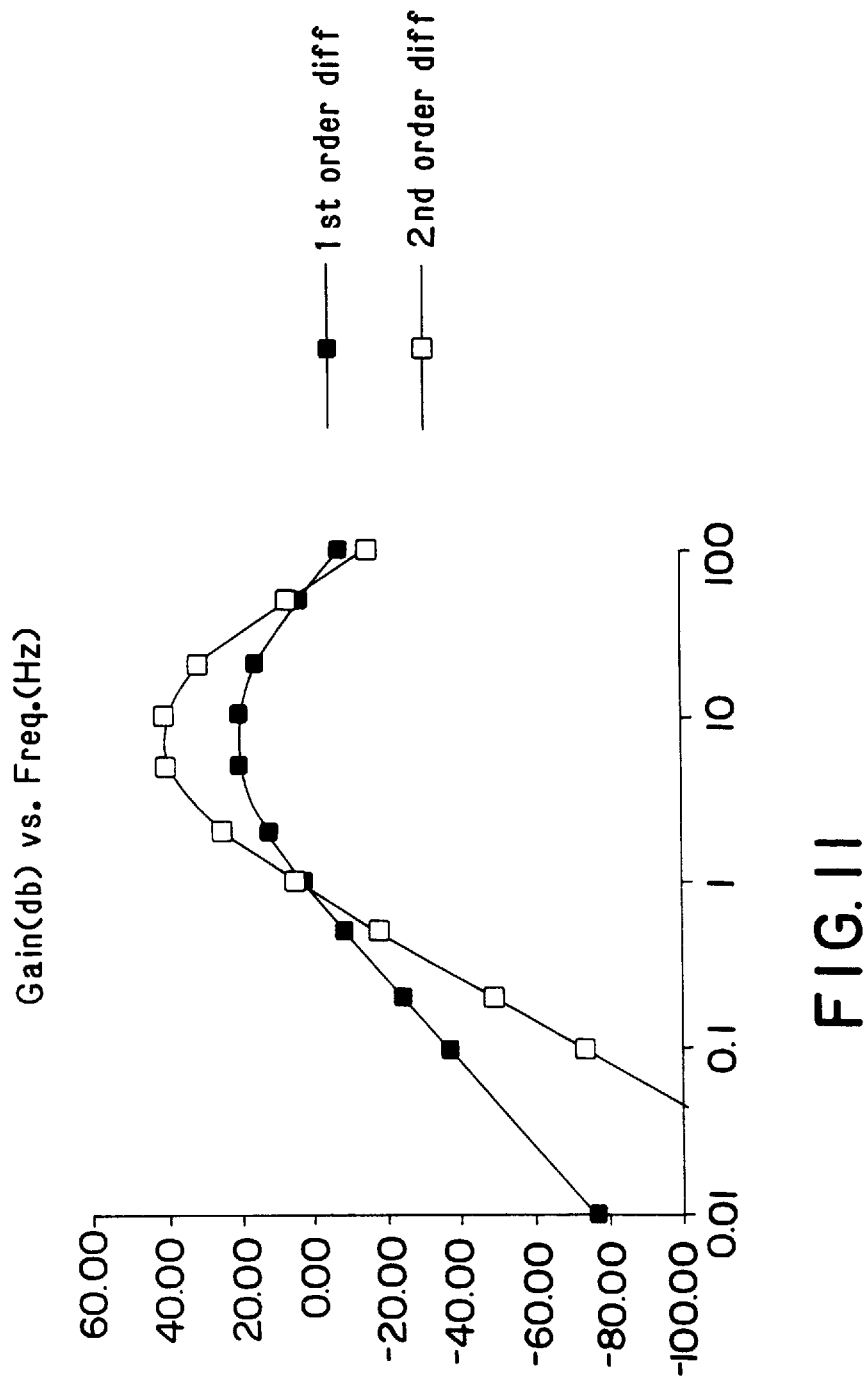

Referring to FIG. 11, integrator 302 (i.e., a second pole) attenuates enhanced signal 94 (i.e., decreasing gain) at higher frequencies. To avoid noise problems the gain is decreased to about zero at approximately 60 Hz.

The characteristic time constant of differentiator/integrator 92 determines the range of frequencies in which the differentiator/integrator will have a peak response. For tissue examination, the relevant range of frequencies is based on the size of any localized areas of stiffer tissue (e.g., lump 30, FIG. 3) to be detected and the speed at which tissue examination device 34 (FIGS. 2 and 3) is moved across tissue 32. Because a user or multiple users will generally move tissue examination device 34 across tissue 32 at different speeds during use, a reasonable range of speeds is assumed.

Figure 12:
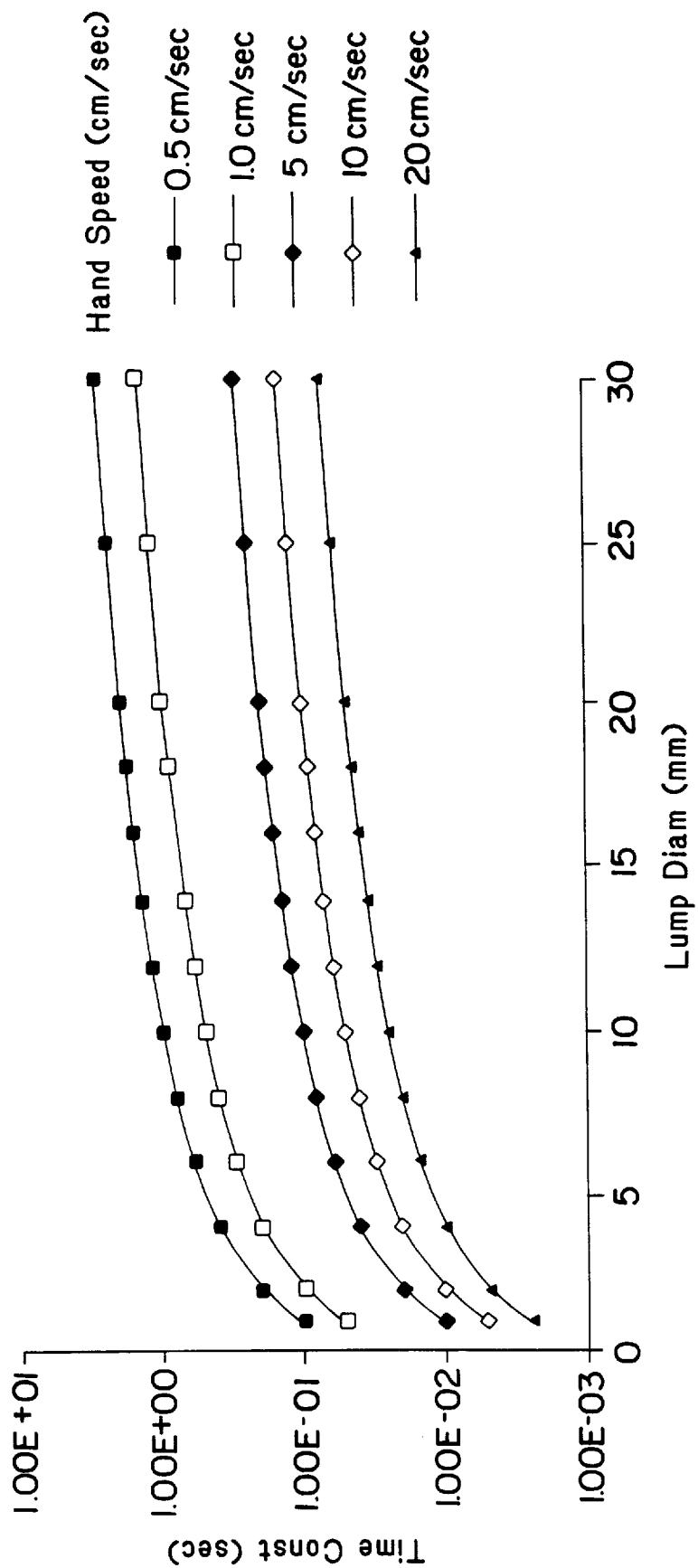

The graph of FIG. 12 represents a model for determining the desired characteristic time constant for differentiator/integrator 92. In this model, the characteristic time constant is based on the time required to cover the slope of a localized area of stiffer tissue and equals the slope of the localized area of stiffer tissue (estimated as one half the diameter of the localized area of stiffer tissue) divided by a predetermined (estimated) tissue examination device speed. For example, for differentiator/integrator 92 to have a peak response for localized areas of stiffer tissue in the range of 5 mm–15 mm when the tissue examination device is moved over the tissue at approximately 5 cm/sec, the model of FIG. 12 indicates that the characteristic time constant for differentiator/integrator 92 should be about 0.1 sec.

Again referring back to FIGS. 6 and 6A–6C output signal 100 from absolute value circuit 98 is a positive signal and threshold signal 104 is a negative signal. Both output signal 100 and threshold signal 104 are connected to pin 12 of U1D within comparator 102. Pin 13 of U1D is connected to ground. Consequently, comparator 102, in effect, compares the difference between output signal 100 and threshold signal 104 to ground. When a sufficiently high rate of change in the difference in force imposed on transducer elements 52, 54 is detected, output signal 100 is sufficiently positive to make the difference between output signal 100 and threshold signal 104 positive (i.e., absolute value circuit 98 pulls-up pin 12 of U1D). As a result, comparator 102 drives output signal 108 high, which causes alarm 110 to illuminate LED 50 to notify the user that a possible localized area of stiffer tissue has been detected. Alarm 110 may also include a piezo buzzer 112 that emits a tone or sound when output signal 108 is driven high by comparator 102.

Figure 10:
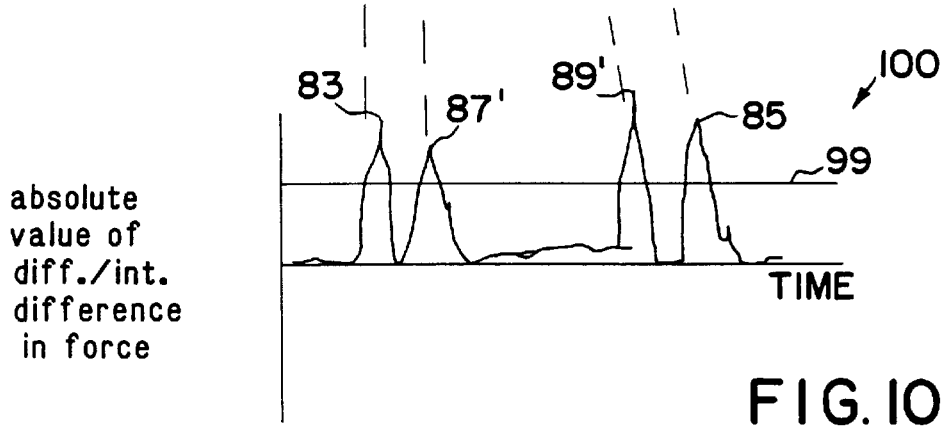

FIG. 10 is a graph of output signal 100 driven by absolute value circuit 98. As shown, absolute value circuit 98 inverts negative peaks 87 and 89 to provide all positive peaks 83, 87', 89', and 85 to comparator 102. Comparator 102 then compares peaks 83, 87', 89', and 85 to single threshold signal 104 (line 99). Because peaks 83, 87', 89', and 85 exceed threshold signal 104, comparator 102 drives output signal 108 high four times to cause alarm 110 to notify the user with four LED 50 pulses (or tones) that a possible localized area of stiffer tissue has been detected.

Threshold signal 104 may be a fixed value or, as shown, may be varied through threshold control circuit 106, e.g., variable resistor 107 connected to a knob (not shown). Threshold control 106 allows a user, preferably a physician with skill and training, to alter threshold signal 104 in accordance with the physiology of a particular user of tissue examination device 34. For example, breast tissue of older women often contains localized areas of stiffer tissue with gradually varying properties (i.e., gradual boundaries), for instance, fibrous structures, calcified milk ducts, or scar tissue. When examining such tissue, a physician may wish to increase threshold signal 104 such that alarm 110 indicates only detected localized areas of stiffer tissue which have quickly changing properties (i.e., sharp boundaries associated with lumps). Conversely, some breast tissue does not contain (or contains very few) localized areas of stiffer tissue with gradually varying properties, and the physician may wish to lower threshold signal 104 such that alarm 110 indicates any detected localized areas of stiffer tissue.

Referring to FIGS. 6 and 6A–6C to determine whether the user is applying sufficient pressure against tissue 32 (FIG. 3) with tissue examination device 34, comparator 114 compares the difference between isolated signal 76 and threshold signal 118 (pin 3 of U4A) to ground (pin 2 of U4A), and comparator 116 compares the difference between isolated signal 78 and threshold signal 120 (pin 12 of U2D) to ground (pin 13 of U2D). Because signals 76 and 78 are inversely proportional to the force applied to transducer elements 54, 52, respectively, as the force decreases, the voltage of signals 76 and 78 become more positive. If the voltage of signal 76 is sufficiently positive (indicating a decrease in force on transducer element 54), the difference between the voltages of signal 76 and threshold signal 118 is positive causing comparator 114 to drive output signal 124 to a positive voltage (i.e., high). Similarly, if the voltage level of signal 78 is sufficiently positive (indicating a decrease in force on transducer element 52), the difference between in the voltage levels of signal 78 and threshold signal 120 is positive causing comparator 116 to drive output signal 126 to a positive voltage level (high). If either output signal 124 or 126 is high, then the user needs to apply more pressure to tissue examination device 34 and alarm 128 notifies the user by lighting LED 48 (and/or causing a piezo buzzer to emit a sound).

Alternatively, variable threshold control 123 (FIG. 5) provides adjustable threshold signal 121. A physician, for instance, may use adjustable threshold signal 121 to modify the pressure threshold in accordance with the physiology of a particular user.

Optionally, jumper 129 (FIG. 6C) connects lockout signal 130 from alarm 128 to alarm 110. If the user is applying insufficient pressure to tissue examination device 34, lockout signal 130 is low and alarm 110 is prevented from notifying a user of lump 30 in tissue 32. This reduces false positive signals that may be generated, for example, when the device is first brought in contact with the tissue.

Other embodiments are within the scope of the following claims.

For example, in addition to detecting whether insufficient pressure is being applied by the user to tissue examination device 34 (FIG. 2, pressure detector 111 (FIG. 5) may also include circuitry for determining whether too much pressure is being applied by the user to tissue examination device 34. The electrical signals 76, 78 may be compared to a minimum threshold and a maximum threshold which establish a range of acceptable levels. If the electrical signals 76, 78 are not within the range of acceptable levels, then alarm 128 notifies the user to increase or decrease the pressure being applied.

Carbon microphone transducer elements 52, 54 may be replaced by any suitable force sensitive elements. Examples include force sensitive resistance transducers based on contact resistance of shunting elements, strain gage based transducers, piezoelectric transducers (e.g., ceramic, electret), capacitive microphone elements, and differential transformers. Additionally, the activated charcoal granules 62 (FIG. 4) may be replaced with saline to provide a saline microphone.

Similarly, transducer elements 52, 54 may be replaced by pressure sensitive elements. For example, one pressure sensitive assembly includes two inflatable pockets or bubbles attached to a differential pressure transducer. As the pockets are pressed against the tissue to be examined, the pockets apply pressure to the differential pressure transducer in accordance with the varying properties of the underlying tissue structure. The differential pressure transducer determines the difference in pressures applied by each pocket, and circuitry similar to that describe above detects variations in the difference in pressures to detect localized areas of stiffer tissue in the tissue being examined.

The signal processing used to detect the boundaries of localized areas of stiffer tissue need not be constrained to determining the rate of change of the difference in the electrical signals generated by the transducer elements. Many variations in the electrical signals generated by the transducer elements may be used to detect localized areas of stiffer tissue, and many methods exist for detecting these variations.

For example, difference signal 86 (FIG. 5) is a periodically varying signal. Periodically varying signals may be reduced through Fourier transforms to the sum of multiple sine waves where each sine wave has a particular frequency, amplitude, and phase angle. Instead of detecting a rate of change of the difference in force applied to each transducer element, the frequency, amplitude, or phase angle of a component of the difference signal may be determined and used to detect localized areas of stiffer tissue.

There are many suitable alternative ways of determining the rate of change of the difference in force imposed on transducer elements 52, 54 over time. For example, the analog circuitry of FIG. 6B may be replaced with different analog circuitry. For instance, differentiator/integrator 92 (FIGS. 5 and 6) may be modified such that the frequency characteristic is replaced by a band-pass filter. Such a circuit also has an increasing gain with increasing frequency followed by a reduction in gain at higher frequencies.

Figure 13:
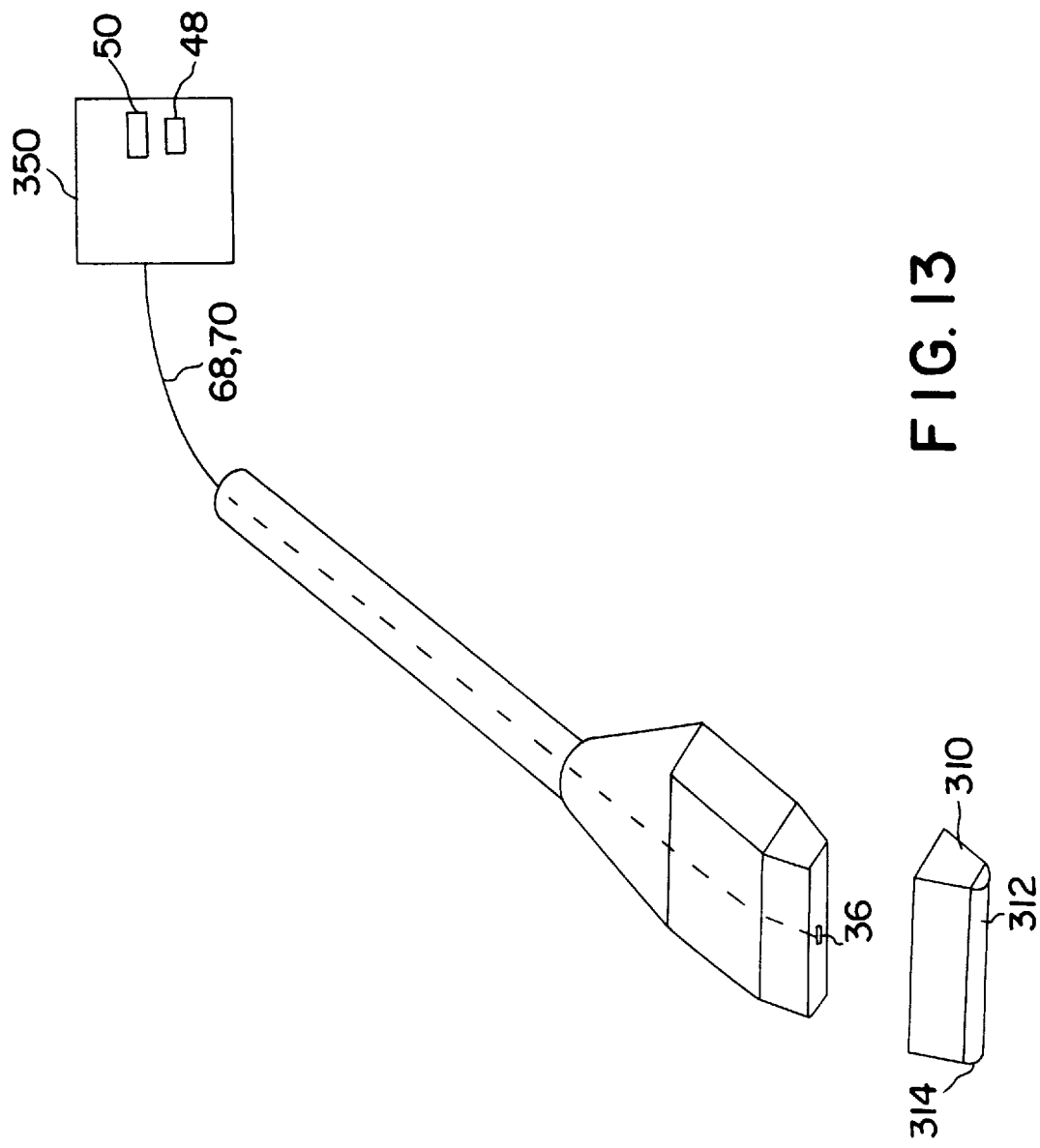
FIG. 13 is a perspective view of another tissue examination device connected to digital circuitry.

Referring to FIG. 13, the analog circuitry of FIGS. 6 and 6A–6C may also be replaced with digital circuitry including a microprocessor and/or a digital signal processor 350 directly connected to transducer assembly 36 through electrical signals 68, 70. The digital circuitry may sample electrical signals 68, 70 from transducer elements 52, 54 and process the sampled data sequentially with, for example, a finite-impulse-response (FIR) filter or similar techniques to enhance the signals. The digital circuitry may then notify the user of any detected possible localized areas of stiffer tissue through LEDs 48, 50.

The digital circuitry may also provide a "learning mode." In the learning mode, an individual user is examined to determine the characteristics of signals corresponding to tissue areas without localized areas of stiffer tissue. These characteristics are then used to determine the thresholds for localized areas of stiffer tissue detection with respect to the individual user. The thresholds and characteristics are then stored in memory (e.g., EEPROM) attached to the microprocessor and/or digital signal processor for use during subsequent examinations.

The analog or digital circuitry may provide a self-test mode. For instance, when the tissue examination device is first powered-up, the circuitry may run a self-test procedure to insure that the circuitry is performing properly. The user may also be involved in the self-test procedure. For example, the user may be signaled (through an LED or sound) to press the transducer assembly against a smooth, flat surface. This allows the circuitry to determine whether the transducer assembly is also performing correctly.

A user or health care professional may compare the results of different exams to determine whether new thickened areas have developed and to determine whether known thickened areas have changed in size. For example, once a thickened area is detected, in the next examination, a user may place the tissue examination device over the same area to determine whether the thickened area has grown. A digital implementation may allow for the storage or permanent record of the results of examinations as well as other information such as date and time of examinations. This information may then be read out at regular intervals to provide a record of longer term trends. This information may also be used to provide an automatic comparison of the results between different examinations.

Comparator 102 (FIG. 5) may further include circuitry for pattern recognition, such as a particular sequence of peaks, e.g., 83, 87', 89', and 85 (FIG. 10). The pattern may be used as a threshold (e.g., a localized area of stiffer tissue is not detected unless the pattern is matched), or the pattern may be used to represent particular types of detected localized areas of stiffer tissue. For example, a pattern for a cyst may be quite different from a pattern for a solid breast lump. Additionally, alarm 110 may notify the user of the particular pattern recognized, for instance, through a series of LEDs or a series of tones or on a display screen.

Figure 14:
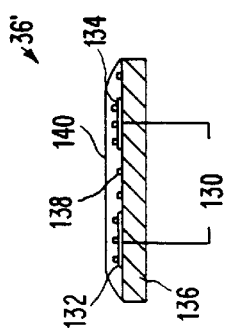
FIG. 14 is a cross-sectional side view of another transducer assembly including a single transducer element.

Referring to FIG. 14, instead of containing dual transducer elements 52, 54 (FIG. 4), transducer assembly 36' may include a single transducer element 130. Single transducer element 130 includes a single pair of electrode strips 132, 134 mounted on an insulating substrate 136, covered with a thin layer of activated charcoal 138, and sealed with a thin plastic coating 140.

Figure 15:
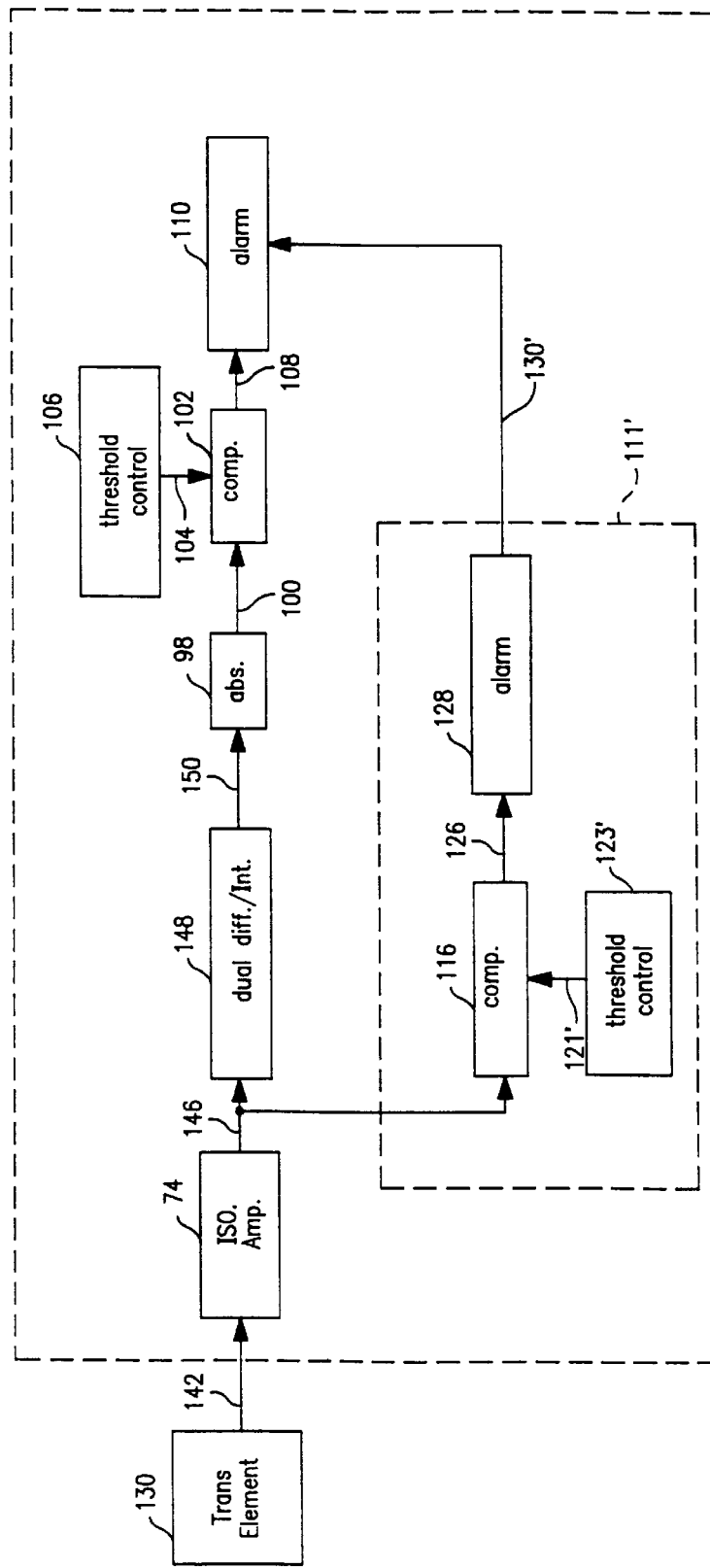
FIG. 15 is a block diagram of another signal processor and the transducer assembly of FIG. 13.

Referring to FIG. 15, transducer element 130 sends a signal 142, that is related to the force imposed on transducer element 130, to an isolation amplifier 74 within signal processor 66'. Output signal 146 of isolation amplifier 74 is operated on by dual differentiator/integrator 148 (dual diff./ int.). The dual differentiator takes the second derivative of output signal 146 and generates enhanced signal 150, approximately:

$$d/dt(df/dt)=d^2f/dt^2.$$

This approximation is similar to the approximation made for enhanced signal 94 (FIGS. 5 and 6B) when transducer elements 52, 54 are used to detect localized areas of stiffer tissue that are larger in diameter than the distance between transducer elements 52, 54. The second order derivative (dual differentiator/integrator) has a transfer function similar to that of a band-pass filter as shown in FIG. 11.

Enhanced signal 150 may be operated on by absolute value circuit 98 in the manner described above with respect to enhanced signal 90. Additionally, comparator 102, threshold control 106, and alarm 110 operate as described above. Signal processor 66' also includes pressure detector 111' which operates in a manner similar to pressure detector 111 (FIG. 5).

Figure 16:
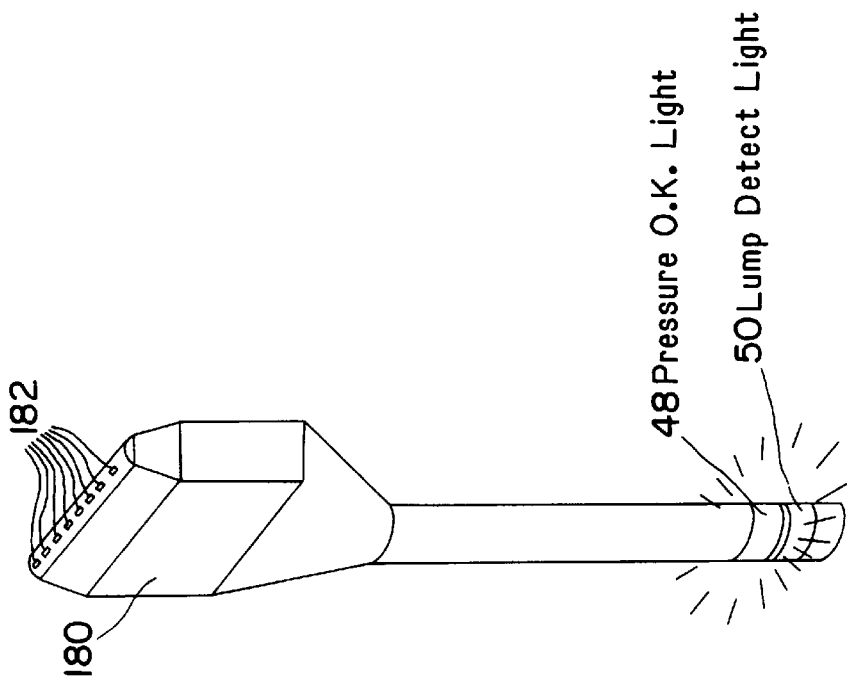
FIG. 16 is a perspective view of yet another tissue examination device including multiple transducer assemblies.

Referring to FIG. 16, tissue examination device 180 may include multiple transducer assemblies 182 including one or more transducer elements. With such an arrangement, the circuitry of signal processor 66 (FIG. 5) or 66' (FIG. 14) is replicated for each transducer assembly 182. Localized area of stiffer tissue alarm 110 may then notify the user (through LED 50 and/or a sound) when any of the transducer assemblies 182 detect a possible localized area of stiffer tissue, e.g., lump 30 (FIG. 3). Alternatively, alarm 110 may include additional circuitry which requires that two or more adjacent transducer assemblies 182 detect a possible localized area of stiffer tissue before the user is notified. This may reduce the number of false positive findings (e.g., where only one transducer assembly 182 or all transducer assemblies 182 in an array of transducer assemblies detects a possible localized area of stiffer tissue, it is probably a false positive finding). Additionally, if more than, for example, six transducer elements of the array detect a signal above the threshold, then the tissue examination device may have detected a large scale structure unrelated to possible localized areas of stiffer tissue, such as a rib. Similarly, if six adjacent transducers detect a signal above the threshold sequentially in time from left to right (or oppositely from right to left), the tissue examination device may be traversing a large scale structure (i.e., a rib or milk duct) at an angle.

Figure 17:
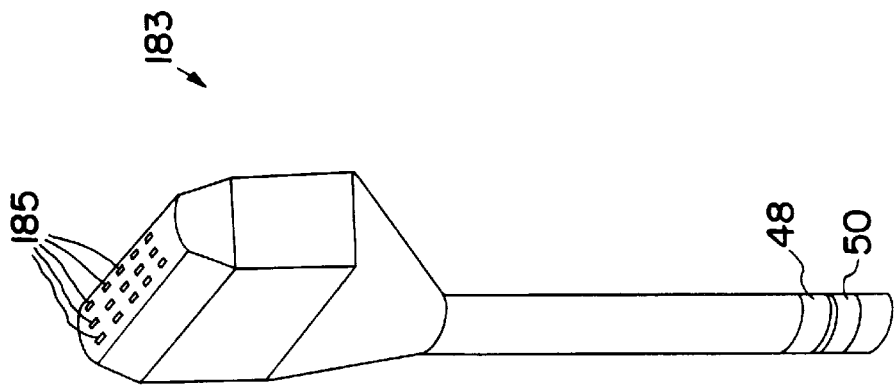
FIG. 17 is a perspective view of yet another tissue examination device including multiple transducer assemblies.

Referring to FIG. 17, tissue examination device 183 may also include multiple transducer assemblies 185 including one or more transducer elements. The transducer assemblies 185 are arranged in a two-dimensional grid, however, many other arrangements are possible.

A configuration of multiple transducer assemblies may allow a more complex pattern recognition methodology to be employed.

Figure 18:
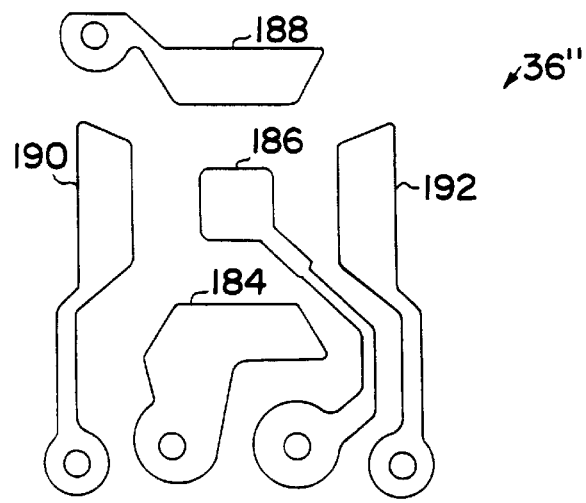
FIG. 18 is a plan view of a transducer assembly including two transducer elements in an orthogonal configuration.

Referring to FIG. 18, transducer assembly 36" may include two (or more) pairs of transducer elements. For instance, one pair of transducer elements includes electrode strips 184, 186, and 188, while another pair of transducer elements includes electrode strips 190, 186, and 192. As shown, these two transducer pairs are orthogonal. The data received from each transducer pair may be compiled by a microprocessor and coordinated with the locations of the transducer pairs with respect to each other to map the location and configuration of any detected localized area of stiffer tissue or boundary of a localized area of stiffer tissue. The signal processing may also be accomplished through an analog circuit. This orthogonal configuration is particularly effective in detecting localized areas of stiffer tissue during the quasi-circular motion recommended for manual breast self-examination.

Figure 19:
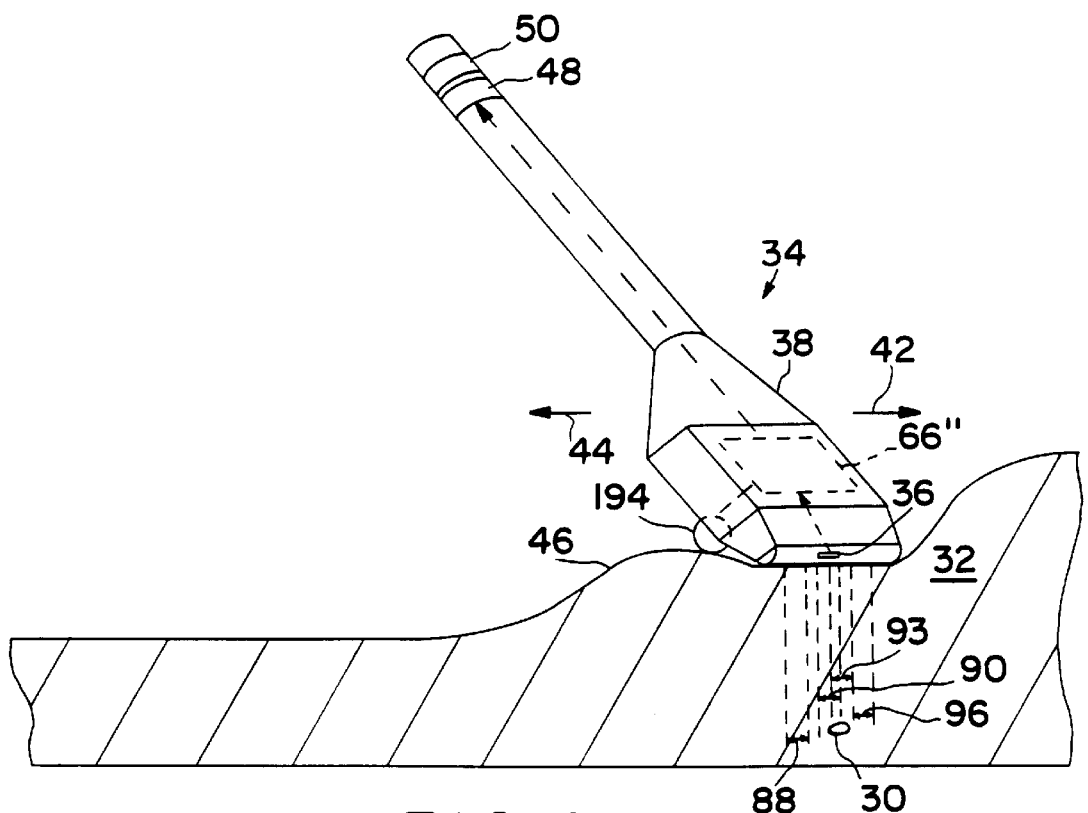
FIG. 19 is a perspective view of yet another tissue examination device including a velocity measuring device.

Referring to FIG. 19, a velocity measuring device, for example, roller ball 194, may also be mounted on housing 38 of tissue examination device 34 and electrically connected to signal processor 66". The measured velocity may be integrated to indicate the position of the tissue examination device with respect to the tissue being examined, and using the measured velocity of the tissue examination device, the signal processor may map out the location of a localized area of stiffer tissue or boundary of a localized area of stiffer tissue within the tissue being examined. Using the measured velocity, the signal processor may also better carry out pattern recognition.

There are many suitable ways to determine the position of the tissue examination device. For instance, the velocity measuring device may be replaced with an accelerometer for measuring the acceleration of the tissue examination device as it is moved over the tissue. The measured acceleration may be integrated twice to indicate the position of the tissue examination device with respect to the tissue being examined. Additionally, the velocity measuring device may be replaced with a position tracking system using, for instance, ultrasound or radio frequency.

An end 38' (FIG. 2) of tissue examination device housing 38 may be rounded and transducer assembly 36 may also be rounded to facilitate movement of the transducer assembly over the tissue to be examined. Additionally, transducer assembly 36 (FIG. 2) may be mounted on a variety of devices designed to facilitate the movement of the transducer assembly across a surface of tissue 32.

Referring to FIG. 20, transducer assembly 36 may be mounted on the outside of finger tip 196 (or any other finger tip) of a glove 198, while signal processor 66 may be secured within housing 200 mounted on wrist 202 of glove 198 (or elsewhere on the glove or separate from the glove). The user, while wearing the glove, nay perform manual breast palpation, which the user may already be familiar and comfortable with, and receive the additional benefits, e.g., small localized area of stiffer tissue detection, of transducer assembly 36. The user's adjacent fingers can be used to detect localized areas of stiffer tissue as in a normal breast self-exam, or one or more of the adjacent fingers of glove 198 may also be mounted with transducer assemblies 36.

Similarly, the transducer assembly may simply be adhered by, for example, an adhesive strip to the user's finger.

There are many suitable ways of detecting force imposed on one or more transducer elements as the tissue examination device is moved across and pressed against the tissue to be examined. For example, referring to FIGS. 19 and 20, tissue examination device 210 includes housing 212 which captures and supports roller ball 214 while still allowing roller ball 214 to turn freely. Three strain instrumented springs 216, 218, and 220 (or similar devices) are attached at one end to a central support member 222 and are attached at the other end to three rollers 224, 226, and 228, respectively. Rollers 224, 226, and 228 roll across a surface of roller ball 214 and are biased toward the surface of the roller ball by strain instrumented springs 216, 218, and 220.

Referring to FIG. 23, each roller 224, 226, 228 (only rollers 224 and 226 are shown) measures the force imposed in a direction perpendicular to the roller ball. As a result, a force vector 224', 226', 228' (only 224' and 226' are shown) is associated with each roller 224, 226, and 228, respectively. If the roller ball is pushed against a flat hard surface, then the resulting force vector 229 (i.e., the combination of force vectors 224', 226', and 228') is vertical and equal to the force imposed on the roller ball. If the roller ball is pushed against and rolled along (arrow 230) a flat hard surface, then the resulting force vector 229' leans (arrow 231) backward due to friction between the roller ball and the surface. When the roller ball is pushed against and moved along tissue to be examined, the resulting force vector angle 232 changes in accordance with the varying properties of the underlying tissue structure. The horizontal component of the resulting force vector is operated upon by processing circuitry 238 to determine force variations in space which indicate possible localized areas of stiffer tissue in the underlying tissue.

Of course, the forces imposed by the roller ball on the rollers may be detected in many ways, including, for example, replacing the strain instrumented springs with simple biasing springs and the rollers with force sensing rollers. Similarly, the roller ball may be biased toward the tissue to be examined through many different mechanisms.

Figure 24:
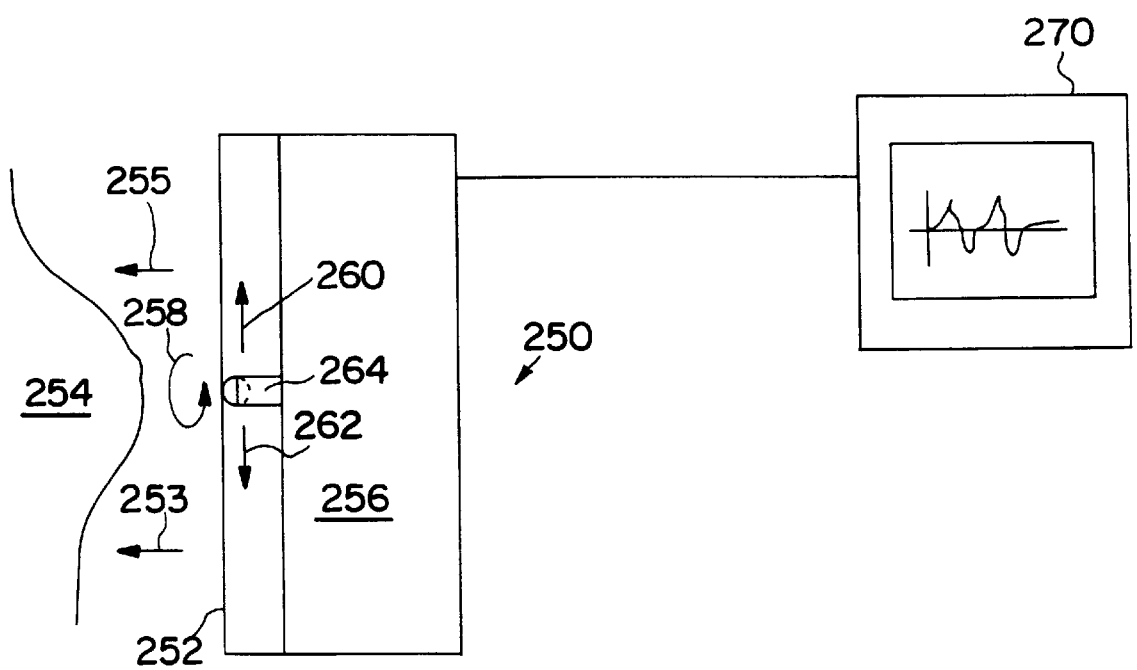
FIG. 24 is a cross-sectional side view of an automatic tissue examination device.

Referring to FIG. 24, instead of a user-movable tissue examination device, an automatic tissue examination device 250 may be provided. Automatic device 250 includes a flexible membrane 252, which is pressed (arrows 253 and 255) against tissue 254 to be examined, and a mechanism 256 for moving (arrows 258, 260, 262) a force sensing device 264, for example, a roller ball configuration similar to that described with respect to FIGS. 21–23. Automatic device 250 may then move the force sensing device across the tissue to be examined at a constant, known velocity in a manner designed to effectively and efficiently examine the tissue.

The above described tissue examination devices may be electrically connected to a display device (e.g., 270, FIG. 24) for displaying information about the electrical signals generated by the transducer elements. The display device may display waveforms, for example, of the type shown in FIGS. 7–10, or the display may show the locations of possible localized areas of stiffer tissue or a map of the tissue being examined.

The above described tissue examination devices may be applied directly to the surface of the tissue to be examined, or the surface of the tissue to be examined may be coated with a lubricant to help the devices glide easily over the tissue surface. Additionally, the devices may be waterproof allowing the device to be used while in the shower or bath tub.

For improved hygienics, a tissue examination device includes a disposable cap 310 (FIG. 13). The cap includes a smooth, thin, e.g., 0.005", flexible plastic sheet 312 on an end 314. Plastic sheet 312 does not substantially impede the force response of transducer assembly 36. Alternatively, transducer assembly 36 is mounted within the disposable cap and includes an electrical connector for connecting the transducer assembly to the tissue examination device when the cap is attached to the tissue examination device.

As previously mentioned, alarm 110 (FIG. 5) may produce an audible tone if a localized area of stiffer tissue is detected. Alternatively, instead of an "on-off" alarm 110, the user may be presented with an analog form of the information. For instance, an audio or visual indicator may continuously produce sound or light and vary that sound or light according to the rate of change (or other variation) of the difference in force imposed on each of the transducer elements. For example, a higher pitched tone (or louder tone) may be produced when the boundary of a localized area of stiffer tissue is crossed. The pitch of the tone may also vary according to the type of localized area of stiffer tissue detected.

Similarly, there are many suitable ways to notify the user that the tissue examination device has detected a localized area of stiffer tissue or insufficient pressure. For example, instead of a sound or light, the tissue examination device could vibrate. Additionally, to insure that the user has received the notification, the light, sound, or vibration may be generated for a fixed period of time.

Movement of tissue examination device 34 (FIG. 2) over tissue 32 is typically accomplished in one of two ways: shear or non-shear movement. Shear movement occurs when tissue examination device 34 moves over tissue 32, as well as, surface 46. In shear movement the dominant deformation strain is compression and shearing stress. Lubrication may assist shear movement. Non-shear movement occurs when friction between tissue examination device 34 and surface 46 does not allow tissue examination device 34 to move over surface 46 but, because the tissue is soft and flexible, tissue examination device 34 still moves over portions of tissue 32. In non-shear movement, the dominant deformation strain is compression and elongation.

The likelihood that a localized area of stiffer tissue will be detected may be increased by establishing different detection thresholds for the two different types of movement, and threshold control 106 (FIG. 5) may be used to adjust the detection threshold in accordance with the planned type of movement. Similarly, processing circuitry 66 may include different localized area of stiffer tissue detection circuitry for the two different types of movement and a mode switch to select between the two different circuits.

The devices described above may be used in a variety of applications. For example, the devices may be used to find localized areas of stiffer tissue in breast tissue, the prostate, the testicles, or the mouth. As another example, the devices may be used to examine the abdomen to find, for example, enlarged ovaries or tumors. As yet another example, the devices may be used to examine tissue to locate arteries or veins for needle placement.

What is claimed is:

1. A tissue examination device comprising:
a transducer element for generating a signal in response to force imposed on the transducer element as the transducer element is pressed against and moved over the tissue, wherein the force varies in accordance with varying properties of an underlying tissue structure; and
circuitry for detecting a variation in the signal generated by the transducer element and for analyzing a shape of said variation between signal levels of different amplitudes to provide an indication of a composition of the underlying tissue structure.

2. The tissue examination device of claim 1, wherein said circuitry comprises:
a processor for performing said analyzing and for determining therefrom whether the transducer element has been moved over a localized area of stiffer tissue within the underlying tissue structure.

3. The tissue examination device of claim 2, further comprising:
circuitry for notifying the user in response to the processor determining that the transducer element has been moved over the localized area of stiffer tissue.

4. The tissue examination device of claim 2, wherein the processor includes:
a comparator for comparing the detected variation in the signal generated by the transducer element to a predetermined threshold to determine whether the transducer element has been moved over the localized area of stiffer tissue within the underlying tissue structure.

5. The tissue examination device of claim 2, wherein the processor includes:
a comparator for comparing the detected variation in the signal generated by the transducer element to a predetermined pattern to determine whether the transducer element has been moved over the localized area of stiffer tissue within the underlying tissue structure.

6. The tissue examination device of claim 1, further comprising:
a pressure sensing circuit, responsive to the signal generated by the transducer element, for detecting whether the force imposed on the transducer element exceeds a predetermined minimum threshold and for notifying the user when the force imposed on the transducer element does not exceed the predetermined minimum threshold.

7. The tissue examination device of claim 1, further comprising:
a pressure sensing circuit, responsive to the signal from the transducer element, for detecting whether the force imposed on the transducer element exceeds a predetermined maximum threshold and for notifying the user when the force imposed on the transducer element exceeds the predetermined maximum threshold.

8. The tissue examination device of claim 1, wherein the transducer element comprises a carbon microphone.

9. A tissue examination device comprising:
a transducer element for generating a signal in response to force imposed on the transducer element as the transducer element is pressed against and moved over the tissue, wherein the force varies in accordance with varying properties of an underlying tissue structure; and
circuitry for detecting a rate of change of the signal generated by the transducer element as an indication of a composition of the underlying tissue structure.

10. The tissue examination device of claim 9, wherein the circuitry includes:
a dual differentiator for determining a second derivative of the signal generated by the transducer element to detect the rate of change of the signal.

11. The tissue examination device of claim 10, wherein the circuitry further includes:
a low pass filter for integrating the second derivative of the signal.

12. The tissue examination device of claim 2 further comprising:
a storage device for storing the results of the processor's determination.

13. The tissue examination device of claim 12 further comprising:
circuitry for comparing the results of different examinations of the same tissue.

14. The tissue examination device of claim 1, further comprising:
a second transducer element for generating a signal in response to force imposed on the second transducer element as the second transducer element is pressed against and moved over the tissue, wherein the force varies in accordance with varying properties of the underlying tissue structure.

15. The tissue examination device of claim 14, wherein the detecting circuitry further detects a variation of the signal generated by the second transducer element as another indication of the composition of the underlying tissue structure.

16. A tissue examination device comprising:
a plurality of transducer elements for generating signals in response to forces imposed on the transducer elements as the transducer elements are pressed against and moved over the tissue, wherein the forces vary in accordance with varying properties of an underlying tissue structure; and
circuitry for detecting a variation in the signals generated by the transducer elements and for analyzing a shape of said variation between signal levels of different amplitudes to provide an indication of a composition of the underlying tissue structure.

17. A tissue examination device comprising:
a plurality of transducer elements for generating signals in response to forces imposed on the transducer elements as the transducer elements are pressed against and moved over the tissue, wherein the forces vary in accordance with varying properties of an underlying tissue structure;
circuitry for detecting a variation in the signals generated by the transducer elements as an indication of a composition of the underlying tissue structure; and
difference circuitry for determining a difference between the signals generated by the transducer elements, wherein the detecting circuitry detects a variation in the difference between the signals generated by the transducer elements.

18. The tissue examination device of claim 16, wherein said circuitry comprises:
a processor for performing said analyzing and for determining therefrom whether at least one transducer element of the plurality of transducer elements has been moved over a localized area of stiffer tissue within the underlying tissue structure.

19. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

circuitry for detecting a variation in the signals generated by the transducer elements as an indication of a composition of the underlying tissue structure; and circuitry for notifying the user in response to the processor determining that at least one transducer element has been moved over the localized area of stiffer tissue.

20. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

circuitry for detecting a variation in the signals generated by the transducer elements as an indication of a composition of the underlying tissue structure; and a processor for determining, based on the detected variation in the signals generated by the transducer elements, whether at least one transducer element of the plurality of transducer elements has been moved over a localized area of stiffer tissue within the underlying tissue structure;

said processor including a comparator for comparing the detected variation in the signals generated by the transducer elements to a predetermined threshold to determine whether at least one transducer element has been moved over the localized area of stiffer tissue within the underlying tissue structure.

21. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure; and circuitry for detecting a variation in the signals generated by the transducer elements as an indication of a composition of the underlying tissue structure; and a processor for determining, based on the detected variation in the signals generated by the transducer elements, whether at least one transducer element of the plurality of transducer elements has been moved over a localized area of stiffer tissue within the underlying tissue structure;

said processor including a comparator for comparing the detected variation in the electrical signals generated by the transducer elements to a variable threshold to determine whether at least one transducer element has been moved over the localized area of stiffer tissue within the underlying tissue structure.

22. The tissue examination device of claim 18, further comprising:

a comparator for comparing the detected variation in the signals generated by the transducer elements to a predetermined pattern to determine whether at least one of the transducer elements has been moved over the localized area of stiffer tissue within the underlying tissue structure.

23. The tissue examination device of claim 18, further comprising:

a comparator for comparing the detected variation in the signals generated by the transducer elements to predetermined patterns to determine whether at least one of the transducer elements has been moved over the localized area of stiffer tissue within the underlying tissue structure and to determine what type of localized area of stiffer tissue the at least one transducer element has been moved over.

24. The tissue examination device of claim 16, further comprising:

a pressure sensing circuit, responsive to the signals generated by the transducer elements, for detecting whether the forces imposed on the transducer elements exceed a predetermined minimum threshold and for notifying the user when the forces imposed on the transducer elements do not exceed the predetermined minimum threshold.

25. The tissue examination device of claim 16, further comprising:

a pressure sensing circuit, responsive to the signals generated by the transducer elements, for detecting whether the forces imposed on the transducer elements exceed a predetermined maximum threshold and for notifying the user when the forces imposed on the transducer elements exceed the predetermined maximum threshold.

26. The tissue examination device of claim 16, further comprising:

a pressure sensing circuit, responsive to the signals generated by the transducer elements, for detecting whether the forces imposed on the transducer elements exceed a variable threshold and for notifying the user when the forces imposed on the transducer elements do not exceed the variable threshold.

27. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

circuitry for detecting a variation in the signals generated by the transducer elements as an indication of a composition of the underlying tissue structure; and a pressure sensing circuit, responsive to the signals generated by the transducer elements, for detecting whether the forces imposed on the transducer elements exceed a variable minimum threshold and whether the forces imposed on the transducer elements exceed a variable maximum threshold, and for notifying the user when the forces imposed on the transducer elements do not exceed the variable minimum threshold or exceed the variable maximum threshold.

28. The tissue examination device of claim 16, wherein the transducer elements comprise carbon microphones.

29. The tissue examination device of claim 16, wherein the transducer elements comprise saline microphones.

30. The tissue examination device of claim 16, wherein the transducer elements comprise piezo-electric elements.

31. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

difference circuitry for determining a difference between the signals generated by the transducer elements; and circuitry for detecting a rate of change of the difference between the signals generated by the transducer elements as an indication of a composition of the underlying tissue structure.

32. The tissue examination device of claim 31, wherein the detecting circuitry includes:

a differentiator for determining a derivative of the difference between the signals generated by the transducer elements to detect the rate of change of the difference between the signals generated by the transducer elements.

33. The tissue examination device of claim 32, wherein the detecting circuitry further includes:

a low pass filter for integrating the derivative of the difference between the signals generated by the transducer elements.

34. The tissue examination device of claim 16, further comprising:

a hand-held assembly, attached to the transducer elements, for moving the transducer elements over the tissue.

35. The tissue examination device of claim 16, further comprising:

a glove, attached to the transducer elements, for moving the transducer elements over the tissue.

36. The tissue examination device of claim 16, further comprising:

an adhesive strip, attached to the transducer elements, for moving the transducer elements over the tissue.

37. The tissue examination device of claim 16, further comprising:

a roller ball assembly, attached to the transducer elements, for moving the transducer elements over the tissue.

38. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

circuitry for detecting a variation in the signals generated by the transducer elements as an indication of a composition of the underlying tissue structure; and a mechanism, attached to the transducer elements, for automatically moving the transducer elements over the tissue.

39. The tissue examination device of claim 17 further comprising:

a storage device for storing the results of the difference circuitry.

40. The tissue examination device of claim 39 further comprising:

circuitry for comparing the results of different examinations of the same tissue.

41. The tissue examination device of claim 17, wherein the plurality of transducer elements comprise a plurality of pairs of transducer elements, and wherein the difference circuitry determines a difference between the signals generated by the transducer elements of each pair of transducer elements and the circuitry for detecting detects a variation in the difference between the signals of each pair of transducer elements as an indication of the composition of the underlying tissue structure.

42. The tissue examination device of claim 41, further comprising:

coordinating circuitry, connected to the plurality of pairs of transducer elements, for coordinating the variations in the differences between the signals of each pair of transducer elements to provide spacial information regarding the location of the localized area of stiffer tissue within the underlying tissue structure.

43. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure; and circuitry for detecting a variation in the signals generated by the transducer elements as an indication of a composition of the underlying tissue structure, wherein the plurality of transducer elements comprise two pairs of transducer elements, the transducer element pairs having an orthogonal configuration with respect to each other, and wherein the difference circuitry determines a difference between the signals generated by the transducer elements of each pair of transducer elements and the circuitry for detecting detects a variation in the difference between the signals of each pair of transducer elements as an indication of the composition of the underlying tissue structure.

44. The tissue examination device of claim 43, further comprising:

coordinating circuitry, connected to the two pairs of transducer elements, for coordinating the variations in the differences between the signals of each pair of transducer elements to provide spacial information regarding the location of the localized area of stiffer tissue within the underlying tissue structure.

45. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure;

circuitry for detecting a variation in the signals generated by the transducer elements as an indication of a composition of the underlying tissue structure;

a processor for determining, based on the detected variation in the signals generated by the transducer elements, whether at least one transducer element of the plurality of transducer elements has been moved over a localized area of stiffer tissue within the underlying tissue structure; and a measuring device for measuring a parameter of the motion of the transducer elements over the tissue.

46. The tissue examination device of claim 45, further comprising:

coordinating circuitry, connected to the measuring device, for coordinating the variations in the difference in the signals generated by the transducer elements to provide spacial information regarding the location of the localized area of stiffer tissue within the underlying tissue structure.

47. The tissue examination device of claims 42, 44, or 46, further comprising:

a display device, connected to the coordinating circuitry, for displaying the location of the localized area of stiffer tissue within the underlying tissue structure.

48. The tissue examination device of claims 3 or 19, wherein the notifying circuitry includes:
   a light emitting diode.

49. The tissue examination device of claims 3 or 19, wherein the notifying circuitry includes:
   a sound generator.

50. The tissue examination device of claims 3 or 18, wherein the localized area of stiffer tissue comprises a lump.

51. A tissue examination device comprising:
   a plurality of transducer elements for generating signals in response to forces imposed on the transducer elements as the transducer elements are pressed against and moved over the tissue, wherein the forces vary in accordance with varying properties of an underlying tissue structure;
   circuitry for detecting a variation in the signals generated by the transducer elements as an indication of a composition of the underlying tissue structure; and
   a cap attached to the tissue examination device.

52. The tissue examination device of claims 1 or 16 further comprising:
   a lubricant disposed between the tissue examination device and the tissue.

53. The tissue examination device of claims 1 or 16, wherein the circuitry for detecting and the processor include analog circuitry.

54. The tissue examination device of claims 1 or 16, wherein the circuitry for detecting and the processor include a microprocessor.

55. The tissue examination device of claims 1 or 16, wherein the tissue is breast tissue.

56. A tissue examination device comprising:
   a plurality of transducer elements for generating signals in response to forces imposed on the transducer elements as the transducer elements are pressed against and moved over the tissue, wherein the forces vary in accordance with varying properties of an underlying tissue structure;
   circuitry for detecting a variation in the signals generated by the transducer elements as an indication of a composition of the underlying tissue structure; and
   self-test circuitry for determining whether the tissue examination device is operating properly.

57. A breast tissue examination device comprising:
   a plurality of transducer elements for generating signals in response to forces imposed on the transducer elements as the transducer elements are pressed against and moved over the breast tissue, wherein the forces vary in accordance with varying properties of an underlying breast tissue structure;
   difference circuitry for determining a difference between the signals generated by the transducer elements;
   circuitry for detecting a variation in the difference between the signals generated by the transducer elements as an indication of a composition of the underlying breast tissue structure;
   a processor for comparing the detected variation in the difference between the signals generated by the transducer elements to a predetermined pattern to determine whether at least one transducer element of the plurality of transducer elements has been moved over a localized area of stiffer tissue within the underlying breast tissue structure; and circuitry for notifying the user in response to the processor determining that at least one transducer element has been moved over the localized area of stiffer breast tissue.

58. A method of examining tissue comprising:
   moving a transducer element over tissue to be examined while also pressing the transducer element against the tissue to be examined, the transducer element generating a signal in response to a force detected by the transducer element, wherein the force varies in accordance with varying properties of an underlying tissue structure; and
   detecting a variation in the signal generated by the transducer element and analyzing a shape of said variation between signal levels of different amplitudes to provide an indication of a composition of the underlying tissue structure.

59. The method of claim 58, further comprising:
   determining, based on said detecting and analyzing, whether the transducer element has been moved over a localized area of stiffer tissue within the underlying tissue structure.

60. The method of claim 59, further comprising:
   notifying the user when the transducer element has been moved over the localized area of stiffer tissue.

61. A method of examining tissue comprising:
   moving a transducer element over tissue to be examined while also dressing the transducer element against the tissue to be examined, the transducer element generating a signal in response to a force detected by the transducer element, wherein the force varies in accordance with varying properties of an underlying tissue structure;
   detecting a variation in the signal generated by the transducer element as an indication of a composition of the underlying tissue structure; and
   comparing the detected variation in the signal generated by the transducer element to a predetermined threshold to determine whether the transducer element has been moved over a localized area of stiffer tissue within the underlying tissue structure.

62. A method of examining tissue comprising:
   moving a transducer element over tissue to be examined while also pressing the transducer element against the tissue to be examined, the transducer element generating a signal in response to a force detected by the transducer element, wherein the force varies in accordance with varying properties of an underlying tissue structure;
   detecting a variation in the signal generated by the transducer element as an indication of a composition of the underlying tissue structure; and
   determining, based on the detected variation in the signal, whether the transducer element has been moved over a localized area of stiffer tissue within the underlying tissue structure; and
   if the transducer element is determined to have been moved over the localized area of stiffer tissue, comparing the detected variation in the signal generated by the transducer element to at least one predetermined pattern to determine what type of localized area of stiffer tissue within the underlying tissue structure the transducer element has been moved over.

63. A method of examining tissue comprising:
   moving a transducer element over tissue to be examined while also pressing the transducer element against the tissue to be examined, the transducer element generating a signal in response to a force detected by the transducer element, wherein the force varies in accordance with varying properties of an underlying tissue structure;

detecting a variation in the signal generated by the transducer element as an indication of a composition of the underlying tissue structure; and comparing the detected variation in the signal generated by the transducer element to a predetermined pattern to determine whether the transducer element has been moved over a localized area of stiffer tissue within the underlying tissue structure.

64. A method of examining tissue comprising:

moving a transducer element over tissue to be examined while also pressing the transducer element against the tissue to be examined, the transducer element generating a signal in response to a force detected by the transducer element, wherein the force varies in accordance with varying properties of an underlying tissue structure; and detecting a rate of change in the signal generated by the transducer element as an indication of a composition of the underlying tissue structure.

65. The method of claim 64, wherein detecting includes:

applying the signal generated by the transducer element to a dual differentiator to detect the rate of change of the signal.

66. The method of claim 65, wherein detecting further includes:

applying the output of the dual differentiator to a low pass filter.

67. The method of claim 59 further comprising:

comparing the determinations as to whether the transducer element has been moved over a localized area of stiffer tissue within the underlying tissue structure between different examinations of the same tissue.

68. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure; and detecting variations in the signals generated by the transducer elements and analyzing a shape of said variations between signal levels of different amplitudes to provide an indication of a composition of the underlying tissue structure.

69. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure;

detecting variations in the signals generated by the transducer elements as an indication of a composition of the underlying tissue structure; and determining a difference between the signals generated by the plurality of transducer elements, wherein detecting variations includes detecting variations in the difference between the signals generated by the plurality of transducer elements.

70. The method of claim 68, wherein detecting includes:

detecting whether at least one of the plurality of transducer elements has been moved over a localized area of stiffer tissue within the underlying tissue structure based on said detecting and analyzing steps.

71. The method of claim 70, further comprising:

notifying the user when at least one of the plurality of transducer elements has been moved over the localized area of stiffer tissue.

72. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure;

determining a difference between the signals generated by the plurality of transducer elements and detecting variations in the difference between said signals as an indication of a composition of the underlying tissue structure; and comparing the detected variations in the difference between the signals generated by the plurality of transducer elements to a predetermined threshold to determine whether at least one of the plurality of transducer elements has been moved over a localized area of stiffer tissue within the underlying tissue structure.

73. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure;

determining a difference between the signals generated by the plurality of transducer elements and detecting variations in the difference between said signals as an indication of a composition of the underlying tissue structure; and comparing the detected variations in the difference between the signals generated by the plurality of transducer elements to a predetermined pattern to determine whether at least one of the plurality of transducer elements has been moved over a localized area of stiffer tissue within the underlying tissue structure.

74. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying Properties of an underlying tissue structure;

determining a difference between the signals generated by the plurality of transducer elements and detecting a rate of change of the difference between said signals as an indication of a composition of the underlying tissue structure.

75. The method of claim 74, wherein determining includes:

applying the difference between the signals to a differentiator.

76. The method of claim 75, wherein determining further includes:

applying the output of the differentiator to a low pass filter.

77. The method of claim 70 further comprising:

comparing the detections as to whether at least one of the transducer elements has been moved over a localized area of stiffer tissue within the underlying tissue structure between different examinations of the same tissue.

78. The method of claims 58 or 68 wherein the tissue is breast tissue.

79. A method of examining tissue comprising:

performing a manual tissue examinations;

thereafter moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure; and detecting variations in the signals generated by the transducer elements as an indication of a composition of the underlying tissue structure.

80. A method of examining tissue comprising:

moving a plurality of transducer elements over tissue to be examined while also pressing the plurality of transducer elements against the tissue to be examined, the transducer elements generating signals in response to forces detected by the transducer elements, wherein the forces vary in accordance with varying properties of an underlying tissue structure;

detecting variations in the signals generated by the transducer elements as an indication of a composition of the underlying tissue structure;

detecting whether at least one of the plurality of transducer elements has been moved over a localized area of stiffer tissue within the underlying tissue structure based on the detected variations in the signals generated by the plurality of transducer elements;

notifying the user when at least one of the plurality of transducer elements has been moved over the localized area of stiffer tissue; and after said notifying, performing a manual tissue examination to re-check the tissue.

81. A method of examining tissue comprising:

initiating a tissue examination device self-test;

moving a plurality of transducer elements of the tissue examination device over tissue to be examined while also pressing the plurality of transducer elements against the tissue to be examined, the transducer elements generating signals in response to forces detected by the transducer elements, wherein the forces vary in accordance with varying properties of an underlying tissue structure; and detecting variations in the signals generated by the transducer elements as an indication of a composition of the underlying tissue structure.

82. A method of examining tissue comprising:

applying lubricant to the tissue in an area to be examined;

moving a plurality of transducer elements over the tissue in said area while also pressing the plurality of transducer elements against the tissue, the transducer elements generating signals in response to forces detected by the transducer elements, wherein the forces vary in accordance with varying properties of an underlying tissue structure; and detecting variations in the signals generated by the transducer elements and analyzing a shape of said variations between signal levels of different amplitudes to provide an indication of a composition of the underlying tissue structure.

83. A method of examining breast tissue comprising:

moving a plurality of transducer elements over the breast tissue to be examined while also pressing the plurality of transducer elements against the breast tissue to be examined, the transducer elements generating signals in response to forces detected by the transducer elements, wherein the forces vary in accordance with varying properties of an underlying breast tissue structure;

detecting variations in the signals generated by the transducer elements as an indication of a composition of the underlying breast tissue structure;

comparing the detected variation in the difference between the signals generated by the plurality of transducer elements to a predetermined pattern to determine whether at least one of the plurality of transducer elements has been moved over the localized area of stiffer tissue within the underlying breast tissue structure; and notifying the user when at least one of the plurality of transducer elements has been moved over the localized area of stiffer tissue.

84. A tissue examination device Ad comprising:

a transducer element for generating a signal in response to force imposed on the transducer element as the transducer element is pressed against and moved over the tissue, wherein the force varies in accordance with varying properties of an underlying tissue structure;

circuitry for detecting a variation in the signal generated by the transducer element and for analyzing a shape of said variation between signal levels of different amplitudes to provide an indication of a composition of the underlying tissue structure; and a cap attached to the tissue examination device.

85. A tissue examination device comprising:

a transducer element for generating a signal in response to force imposed on the transducer element as the transducer element is pressed against and moved over the tissue, wherein the force varies in accordance with varying properties of an underlying tissue structure;

circuitry for detecting a variation in the signal generated by the transducer element and for analyzing a shape of said variation between signal levels of different amplitudes to provide an indication of a composition of the underlying tissue structure; and self-test circuitry for determining whether the tissue examination device is operating properly.

86. A method of examining tissue comprising:

performing a manual tissue examination;

thereafter moving a transducer element over tissue to be examined while also pressing the transducer element against the tissue to be examined, the transducer element generating a signal in response to a force detected by the transducer element, wherein the force varies in accordance with varying properties of an underlying tissue structure; and detecting a variation in the signal generated by the transducer element and analyzing a shape of said variation between signal levels of different amplitudes to provide an indication of a composition of the underlying tissue structure.

87. A method of examining tissue comprising:

moving a transducer element over tissue to be examined while also pressing the transducer element against the tissue to be examined, the transducer element generating a signal in response to a force detected by the transducer element, wherein the force varies in accordance with varying properties of an underlying tissue structure;

detecting a variation in the signal generated by the transducer element as an indication of a composition of the underlying tissue structure;

determining, based on the detected variation in the signal, whether the transducer element has been moved over a localized area of stiffer tissue within the underlying tissue structure;

notifying the user when the transducer element has been moved over the localized area of stiffer tissue; and after said notifying, performing a manual tissue examination to re-check the tissue.

88. A method of examining tissue comprising:

initiating a tissue examination device self-test;

moving a transducer element of the tissue examination device over tissue to be examined while also pressing the transducer element against the tissue to be examined, the transducer element generating a signal in response to a force detected by the transducer element, wherein the force varies in accordance with varying properties of an underlying tissue structure; and detecting a variation in the signal generated by the transducer element and analyzing a shape of said variation between signal levels of different amplitudes to provide an indication of a composition of the underlying tissue structure.

89. A method of examining tissue comprising:

applying lubricant to the tissue in an area to be examined;

moving a transducer element over the tissue in such area while also pressing the transducer element against the tissue, the transducer element generating a signal in response to a force detected by the transducer element, wherein the force varies in accordance with varying properties of an underlying tissue structure; and detecting a variation in the signal generated by the transducer element and analyzing a shape of said variation between signal levels of different amplitudes to provide an indication of a composition of the underlying tissue structure.

90. The tissue examination device of claim 45 wherein the parameter of motion includes a velocity of the transducer elements.

91. The tissue examination device of claim 45 wherein the parameter of motion includes a change in a position of the transducer elements with respect to the tissue being examined.

92. The tissue examination device of claim 51 or 84 wherein said cap is disposable.

93. The tissue examination device of claim 1 further comprising a hand-held housing that contains said transducer element and said circuitry.

94. The tissue examination device of claim 16 further comprising a hand-held housing that contains said plurality of transducer elements and said circuitry.

95. Apparatus comprising a tissue examination device that includes a transducer element and that is configured to press said transducer element against the tissue and move said transducer element over the tissue to cause said transducer element to generate a signal in response to force imposed on the transducer element as the transducer element is pressed against and moved over the tissue, such force varying in accordance with varying properties of an underlying tissue structure; and circuitry associated with said tissue examination device for detecting a variation in the signal generated by the transducer element and for analyzing a share of said variation between signal levels of different amplitudes to provide an indication of a composition of the underlying tissue structure.

96. Apparatus comprising a tissue examination device that includes a plurality of transducer elements and that is configured to press said transducer elements against the tissue and move said transducer elements over the tissue to cause said transducer elements to generate signals in response to forces imposed on the transducer elements as the transducer elements are pressed against and moved over the tissue, such forces varying in accordance with varying properties of an underlying tissue structure; and circuitry associated with said tissue examination device for detecting a variation in the signals generated by the transducer elements and for analyzing a shape of said variation between signal levels of different amplitudes to provide an indication of a composition of the underlying tissue structure.

97. A tissue examination device comprising:

a transducer element for generating a signal in response to force imposed on the transducer element as the transducer element is pressed against and moved over the tissue, wherein the force varies in accordance with varying properties of an underlying tissue structure; and circuitry for detecting as a function of the movement of said transducer element a variation in the signal generated by the transducer element and for analyzing a shape of said variation between signal levels of different amplitudes to provide an indication of a composition of the underlying tissue structure.

98. A tissue examination device comprising:

a plurality of transducer elements for generating signals in response to forces imposed on the transducer elements as the transducer elements are pressed against and moved over the tissue, wherein the forces vary in accordance with varying properties of an underlying tissue structure; and circuitry for detecting as a function of the movement of said transducer elements a variation in the signals generated by the transducer elements and for analyzing a shape of said variation between signal levels of different amplitudes to provide an indication of a composition of the underlying tissue structure.

99. A method of examining tissue comprising:

pressing and moving a transducer element along the tissue to be examined while maintaining the transducer element in substantially continuous contact with the tissue to cause the transducer element to generate a signal in response to a force detected by the transducer element, such force varying in accordance with varying properties of an underlying tissue structure; and detecting a variation in the signal generated by the transducer element and analyzing a shape of said variation between signal levels of different amplitudes to provide an indication of a composition of the underlying tissue structure.

100. A method of examining tissue comprising:

pressing and moving a plurality of transducer elements along the tissue to be examined while maintaining the transducer elements in substantially continuous contact with the tissue to cause the transducer elements to generate signals in response to a force detected by the transducer element, such force varying in accordance with varying properties of an underlying tissue structure; and detecting a variation in the signals generated by the transducer elements and analyzing a shape of said variation between signal levels of different amplitudes to provide an indication of a composition of the underlying tissue structure.

101. A tissue examination device comprising:

a transducer element for generating signals in response to forces imposed on the transducer element as the transducer element is pressed against and moved over the tissue, wherein the forces vary in accordance with varying properties of an underlying tissue structure; and circuitry for detecting a variation in the signal generated by the transducer element, for analyzing a shape of said variation between signal levels of different amplitudes, and for detecting therefrom that said transducer element has been moved over an edge of the underlying tissue structure.

102. A tissue examination device comprising a plurality of transducer elements for generating signals in response to forces imposed on the transducer elements as the transducer elements are pressed against and moved over the tissue, wherein the forces vary in accordance with varying properties of an underlying tissue structure; and circuitry for detecting a variation in the signals generated by the transducer elements, for analyzing a shape of said variation between signal levels of different amplitudes, and for detecting therefrom that at least one of said transducer elements has been moved over an edge of the underlying tissue structure.

103. A method of examining tissue comprising:

moving a transducer element over the tissue to be examined while also pressing the transducer element against the tissue to cause the transducer element to generate a signal in response to a force detected by the transducer element, such force varying in accordance with varying properties of an underlying tissue structure; and detecting a variation in the signal generated by the transducer element, analyzing a shape of said variation between signal levels of different amplitudes, and detecting therefrom that said transducer element has been moved over an edge of the underlying tissue structure.

104. A method of examining tissue comprising:

moving a plurality of transducer elements over the tissue to be examined while also pressing the transducer elements against the tissue to cause the transducer elements to generate signals in response to a force detected by the transducer element, such force varying in accordance with varying properties of an underlying tissue structure; and detecting a variation in the signals generated by the transducer elements, analyzing a shape of said variation between signal levels of different amplitudes, and detecting therefrom that at least one of said transducer elements has been moved over an edge of the underlying tissue structure.

* * * * *

UNITED STATES PATENT AND TRADEMARK OFFICE
CERTIFICATE OF CORRECTION

PATENT NO. : 5,833,634

DATED : November 10, 1998

INVENTOR(S) : John D. Laird et al.

Figure 6A:
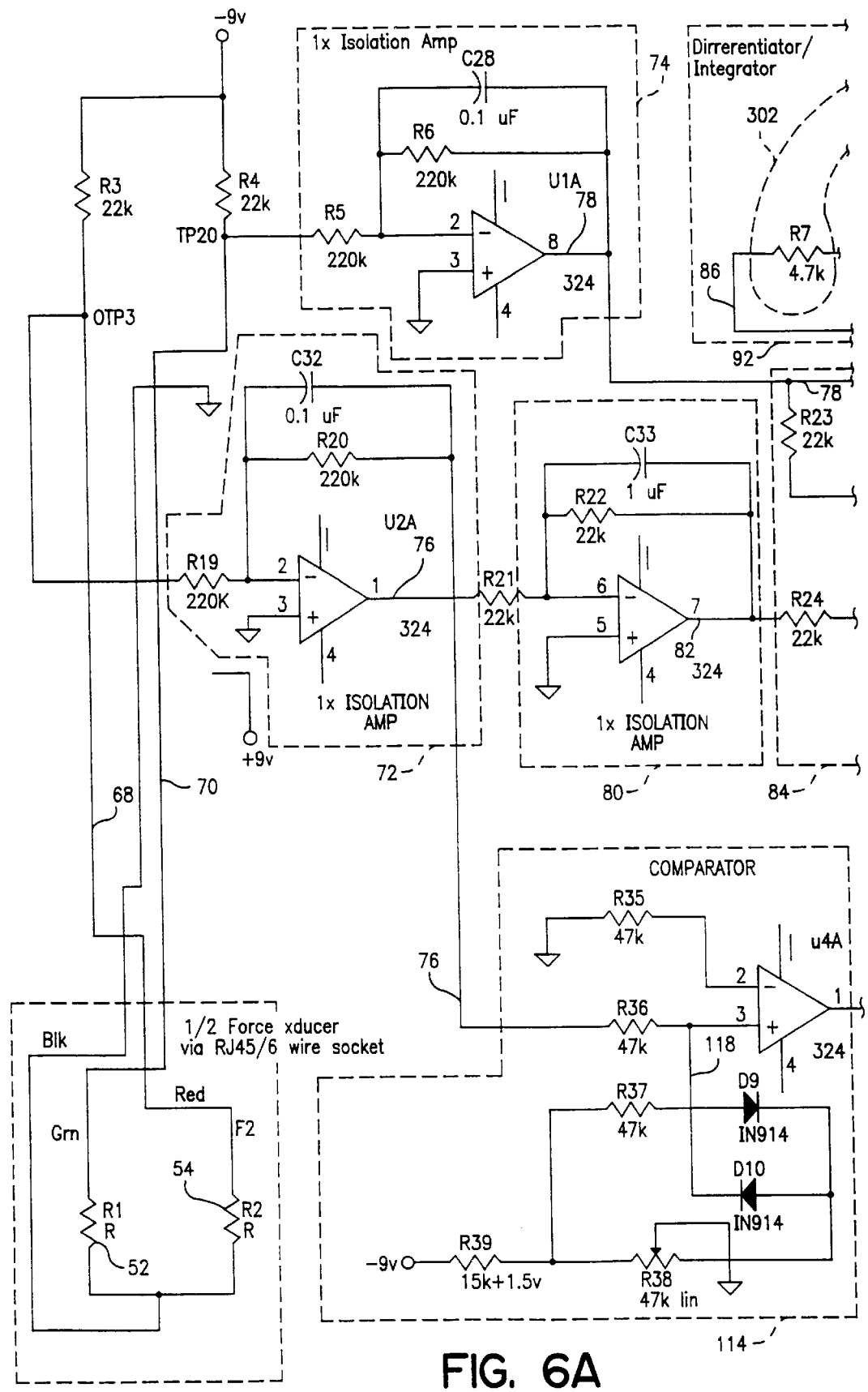
Figure 6C:
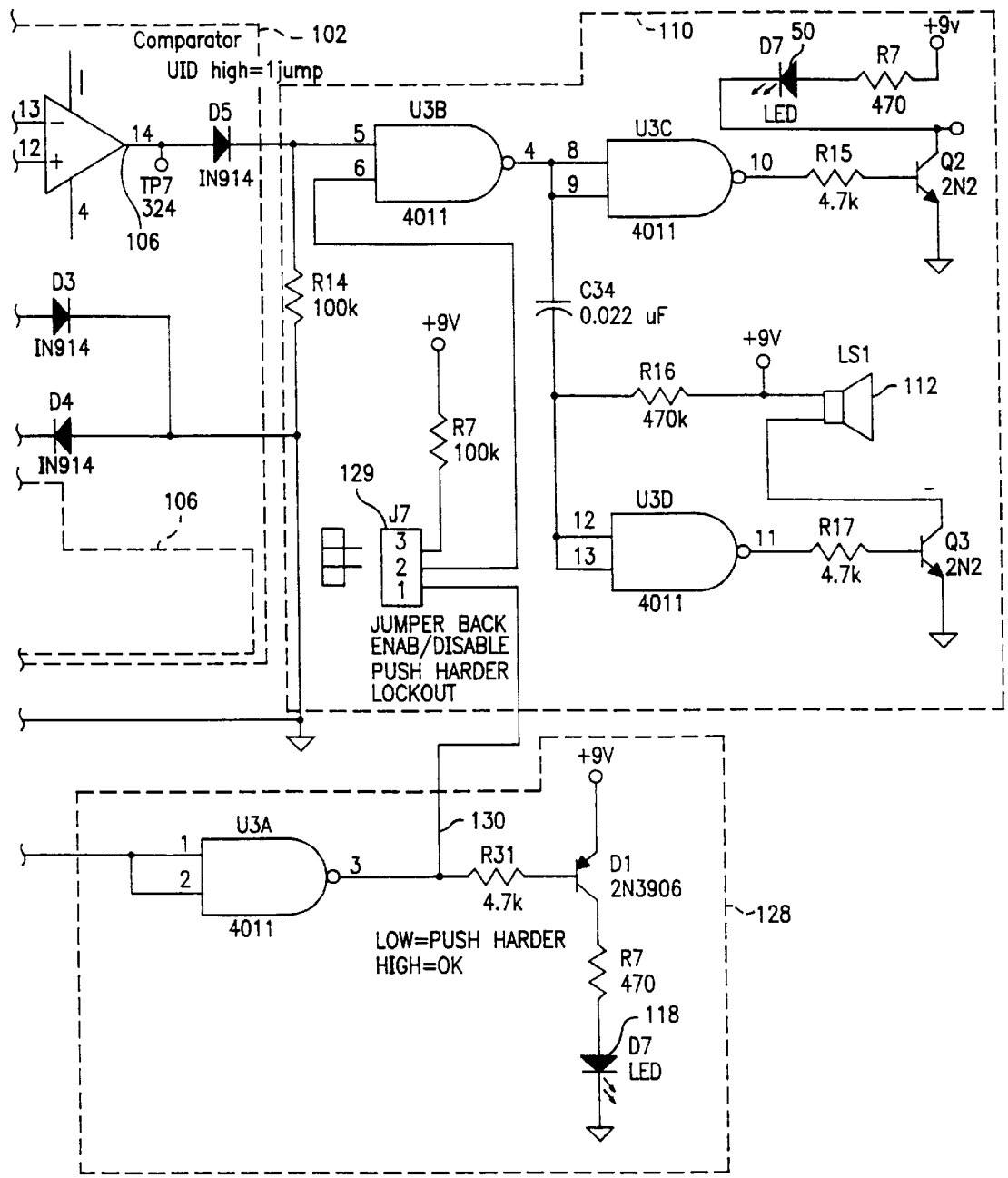

It is certified that error appears in the above-identified patent and that said Letters Patent is hereby corrected as shown below:

Col. 10, line 27, replace "FIG. 6B" with --FIGS. 6 and 6A-6C--.

Col. 10, line 29, replace "6" with --6B--.

Col. 24, claim 74, line 55, replace "Properties" with --properties--.

Col. 25, claim 79, line 11, replace "examinations;" with --examinations--.

Col. 26, claim 84, line 28, delete "Ad".

Col. 29, claim 102, line 29, replace "comprising" with --comprising:--

Signed and Sealed this

Fifteenth Day of June, 1999

Attest:

Q. TODD DICKINSON

*Attesting Officer*    *Acting Commissioner of Patents and Trademarks*